US009095624B2

(12) United States Patent
Sobolev et al.

(10) Patent No.: US 9,095,624 B2
(45) Date of Patent: Aug. 4, 2015

(54) MODULAR TRANSPORT PLATFORM FOR TARGETED DELIVERY OF THERAPEUTIC AGENTS

(75) Inventors: Alexander S. Sobolev, Moscow (RU); Andrey A. Rosenkranz, Moscow (RU); David A. Jans, Caulfield Sth. (AU); Vladimir G. Lunin, Moscow (RU)

(73) Assignee: Contango Partners Group, Inc., Belize (BZ)

( * ) Notice: Subject to any disclaimer, the term of this patent is extended or adjusted under 35 U.S.C. 154(b) by 0 days.

(21) Appl. No.: 13/371,377

(22) Filed: Feb. 10, 2012

(65) Prior Publication Data

US 2013/0045533 A1 Feb. 21, 2013

Related U.S. Application Data

(60) Provisional application No. 61/489,181, filed on May 23, 2011, provisional application No. 61/528,971, filed on Aug. 30, 2011.

(51) Int. Cl.

| | |
|---|---|
| ***A61K 31/40*** | (2006.01) |
| ***A61K 38/41*** | (2006.01) |
| ***A61K 51/00*** | (2006.01) |
| ***A61K 47/48*** | (2006.01) |
| ***A61K 41/00*** | (2006.01) |
| ***A61K 51/08*** | (2006.01) |

(52) U.S. Cl.

CPC ....... *A61K 47/48269* (2013.01); *A61K 41/0071* (2013.01); *A61K 47/48261* (2013.01); *A61K 47/48307* (2013.01); *A61K 51/081* (2013.01); *A61K 51/088* (2013.01)

(58) Field of Classification Search

None

See application file for complete search history.

(56) References Cited

U.S. PATENT DOCUMENTS

| | | | | |
|---|---|---|---|---|
| 6,500,800 | B1 * | 12/2002 | Sobolev et al. ................ | 514/1.2 |
| 6,534,040 | B2 * | 3/2003 | Pandey et al. .............. | 424/9.362 |
| 2009/0068736 | A1 * | 3/2009 | Veeraraghavan et al. ..... | 435/375 |

OTHER PUBLICATIONS

Sobolev. Novel modular transporters delivering anticancer drugs and foreign DNA to the nuclei of target cancer cells. J Buon. Sep. 2009; 14(Suppl 1): S33-S42.*

Ioannidis et al., Spectroscopic studies on an oxygen-binding haemoglobin-like f1avohaemoprotein from *Escherichia coli*. Biochem. J. (1992) 288, 649-655.*

Sobolev. Modular transporters for subcellular cell-specific targeting of anti-tumor drugs. BioEssays 30:278-287, 2008.*

Gilyazova et al., Recombinant modular transporters on the basis of epidermal growth factor for targeted intracellular delivery of photosensitizers. Proc. SPIE 5973, Current Research on Laser Use in Oncology: 2000-2004, 59730E (Dec. 7, 2006); p. 1-10.*

Oliveira et al., Synthesis of new amphiphilic chlorin derivatives from protoporphyrin-IX dimethyl ester. Tetrahedron 64 (2008) 8709-8715.*

Pandey et al., Synthesis, photophysical properties, in vivo photosensitizing efficacy, and human serum albumin binding properties of some novel bacteriochlorins. J Med Chem. Aug. 15, 1997;40(17):2770-9.*

* cited by examiner

*Primary Examiner* — Kevin Hill
*Assistant Examiner* — Arthur S Leonard
(74) *Attorney, Agent, or Firm* — William D. Hare; McNeely, Hare & War, LLP

(57) ABSTRACT

The invention relates to a modular transport platform (MTP) configured to penetrate a target cell, deliver the MTP into the target cell, provide a pH dependent membrane disruption activity, direct intracellular transport into a target subcellular compartment of the target cell, and couple the active agent within the modular platform. The modular transport platform includes: (1) a ligand module to target a specific receptor on the surface of the target cell; (2) an endosomolytic module that provides pH-dependent membrane disruption activity within the target cell; (3) an intracellular transport module to cause delivery of the MTP to a particular subcellular compartment; (4) a module for intracellular retention; (5) a module for subcellular recognition; (6) a substance to be transported by the MTP; and (7) a carrier module for unifying the modules and coupling the modules with the transported substance.

15 Claims, 13 Drawing Sheets

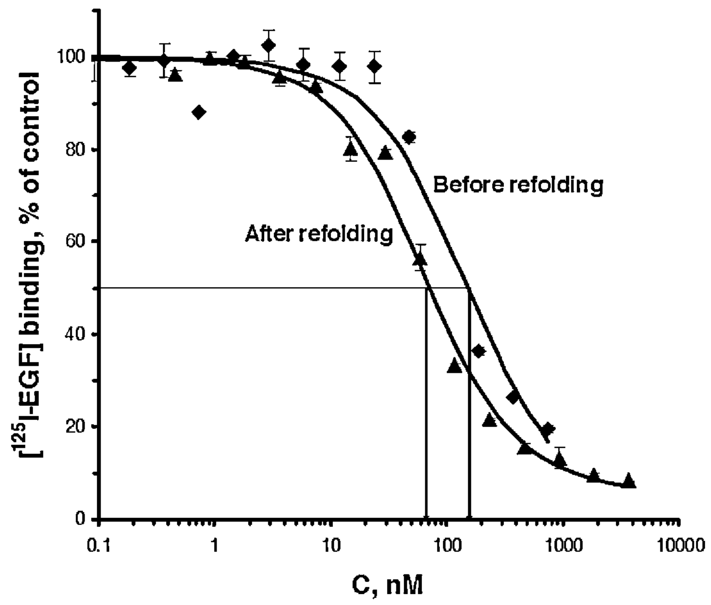

Fig. 1. Effect of MTP posttranslational treatment on affinity of its ligand module to cell receptor. Displacement of [$^{125}$I]iodo-EGF (2 nM) by DTox-HMP-NLS-EGF before (◆) and after (▲) refolding from EGFR receptors of A431 human epidermoid carcinoma cells. [$^{125}$I]iodo-EGF bound to A431 cell surface receptors with affinity constant of 0.15±0.02 $nM^{-1}$. Affinity constants for MTP binding with receptor were 0.019±0.003 $nM^{-1}$ before refolding and 0.054±0.005 $nM^{-1}$ after refolding.

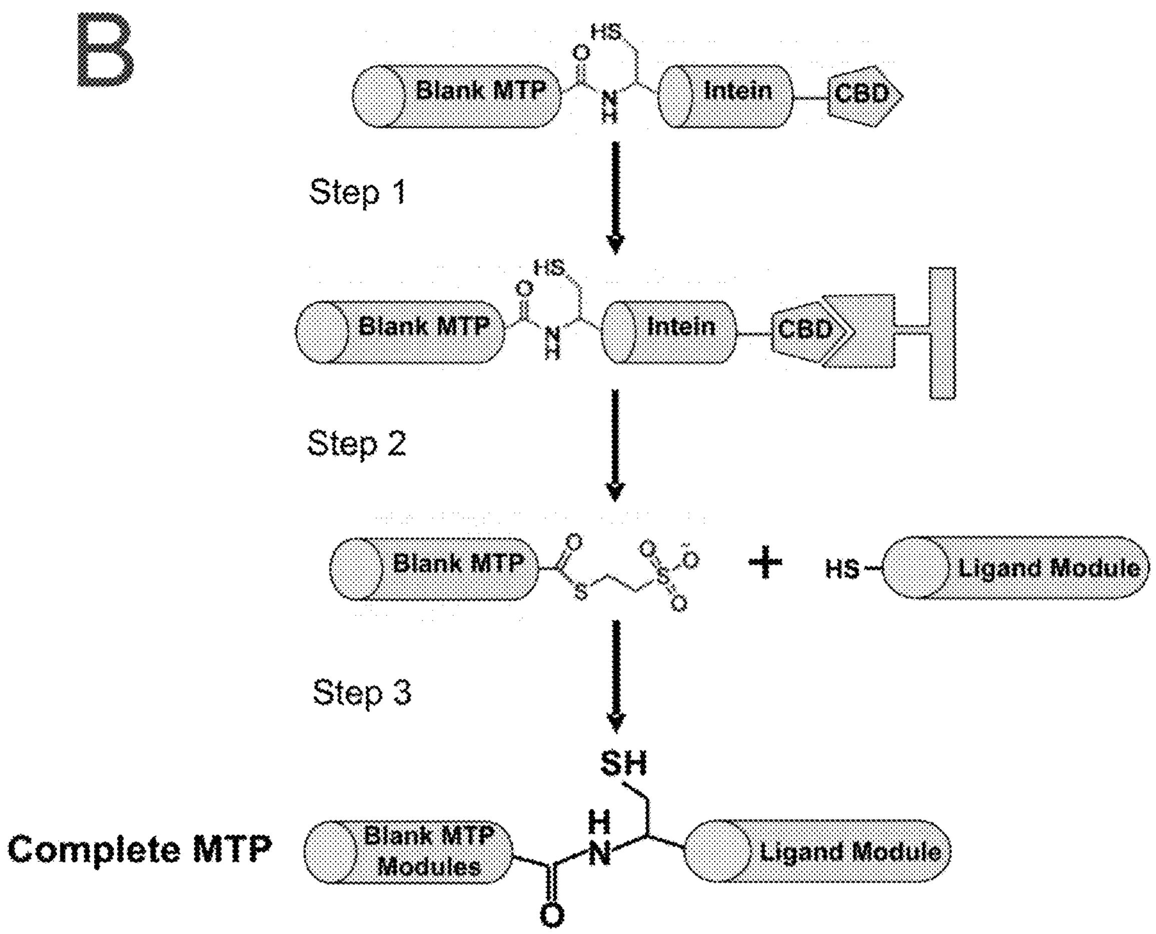
Fig. 2. Schematic representation of construction of an MPT encoding plasmid possessing intein and CBD (chitin-binding domain)-encoding regions, purification of the "blank" MTP, and the liganding step of the non-liganded MTP to the polypeptide ligand.

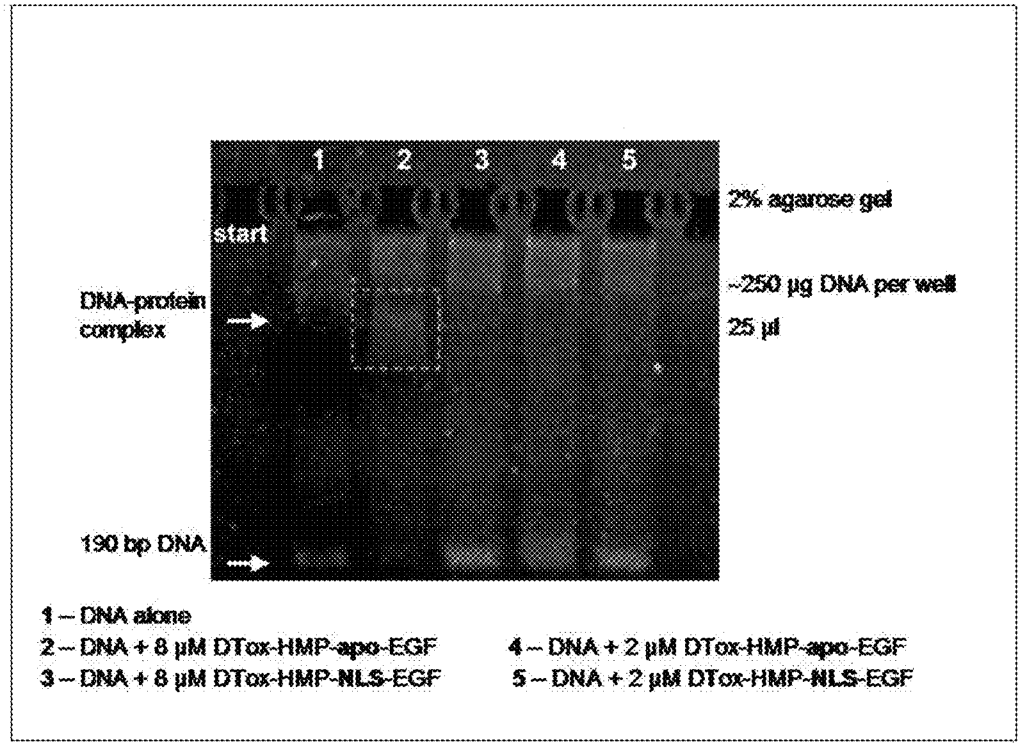
Fig. 3. Gel-shift assay with MTP containing apoptin fragment, DTox-HMP-apo-EGF, and lacking it, DTox-HMP-NLS-EGF.

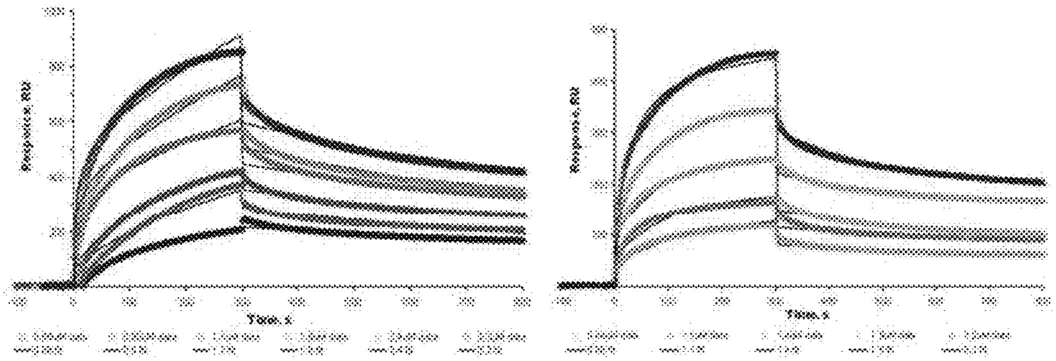
Fig. 4. the interaction of DTox-HMP-apo-EGF (left graph) and DTox-HMP-NLS-EGF (right graph) with plasmid DNA assayed using surface plasmon resonance method on SA chip. Affinity constants for MTP binding with DNA were 0.26±0.06 $\mu M^{-1}$ for DTox-HMP-apo-EGF and 0.011±0.002 $\mu M^{-1}$ for DTox-HMP-NLS-EGF.

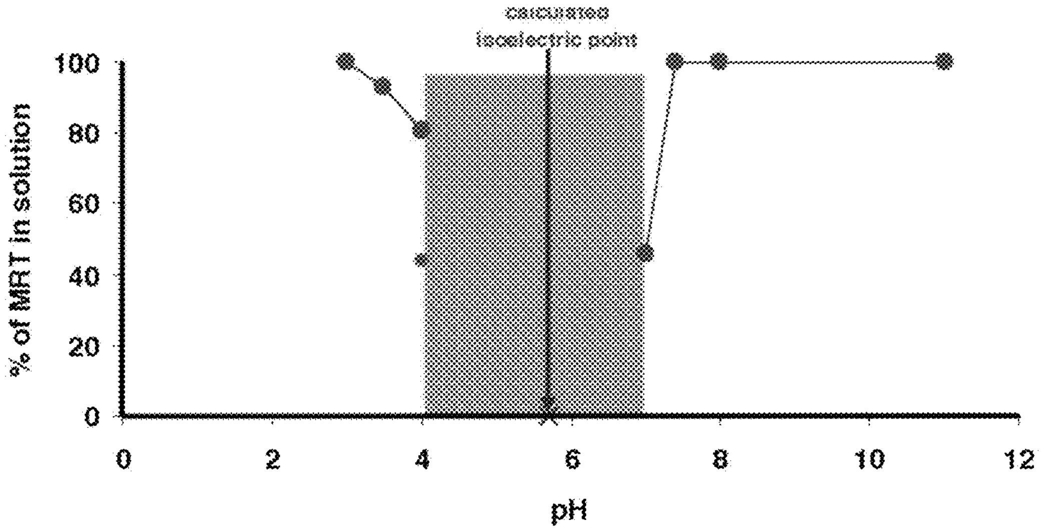
Fig. 5. Solubility of MTP at different pH conditions

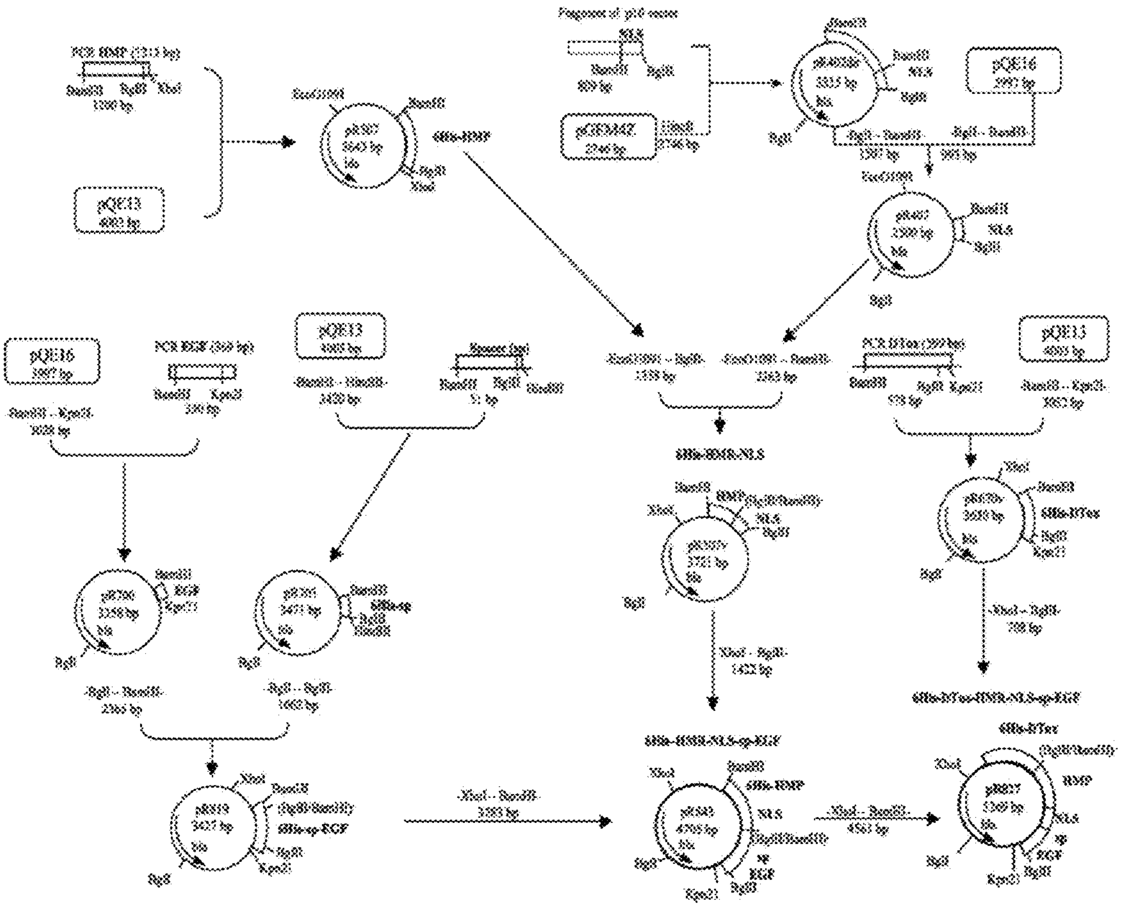
Fig. 6. Schematic representation of plasmid construction to create the plasmid pR827 encoding the EGF-containing MTP DTox-HMP-NLS-EGF.

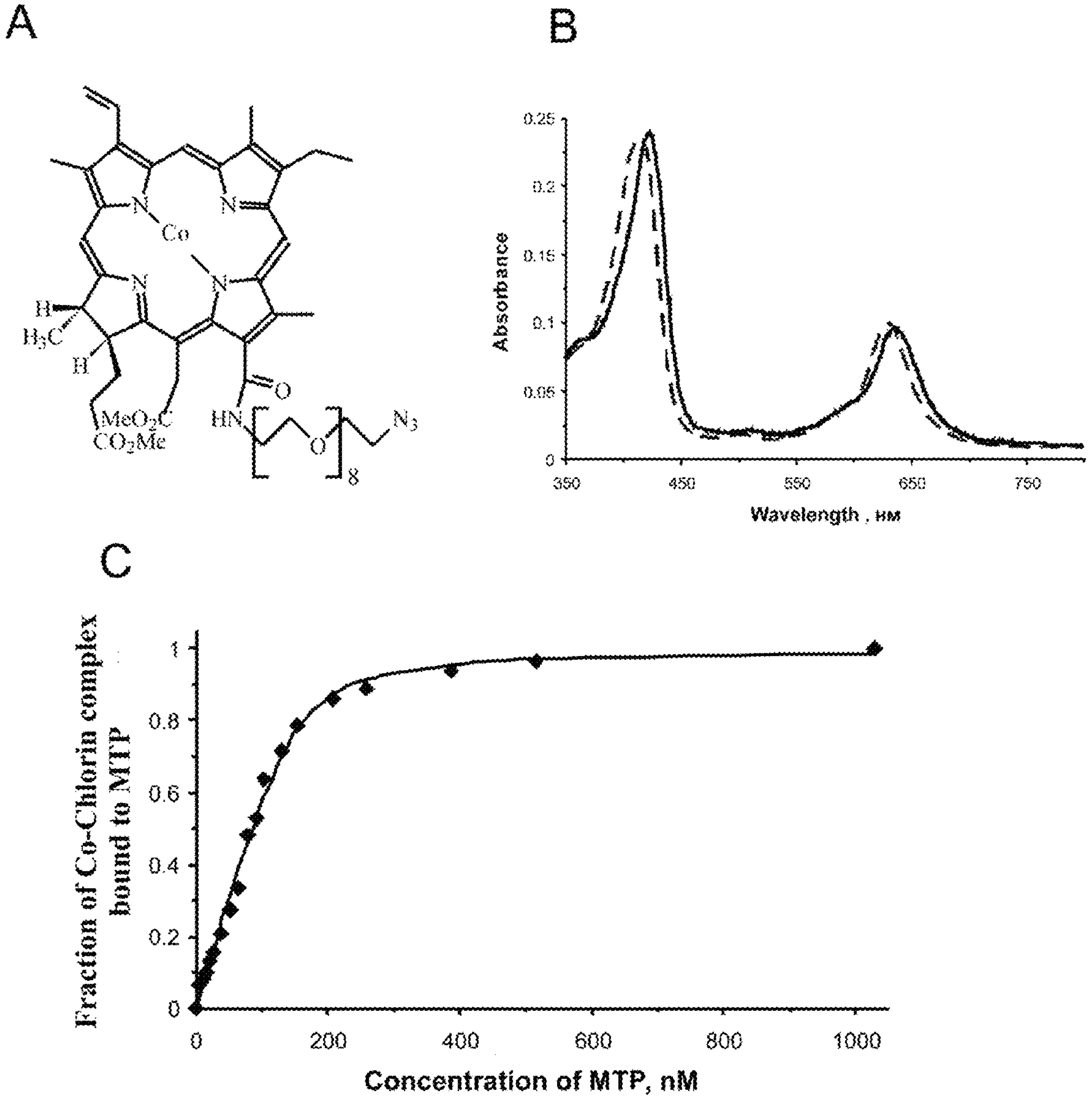

Fig. 7. Insertion of chlorine derivative into MTP. A – azido-polyethylene glycol derivative of Co-chlorin complex (Co-Chl-PEG-$N_3$); B – absorption spectra of Co-Chl-PEG-$N_3$ (dashed line) and complex of Co-Chl-PEG-$N_3$ with DTox-HMP-NLS-MSH MTP (full line) in 10 mM sodium phosphate pH 8.0; C – the dependence of bound Co-Chl-PEG-$N_3$ share on MRT concentration calculated from MTP-Co-Chl-PEG-$N_3$ spectra by nonlinear regression from Soret bands of complexes at different MTP concentrations.

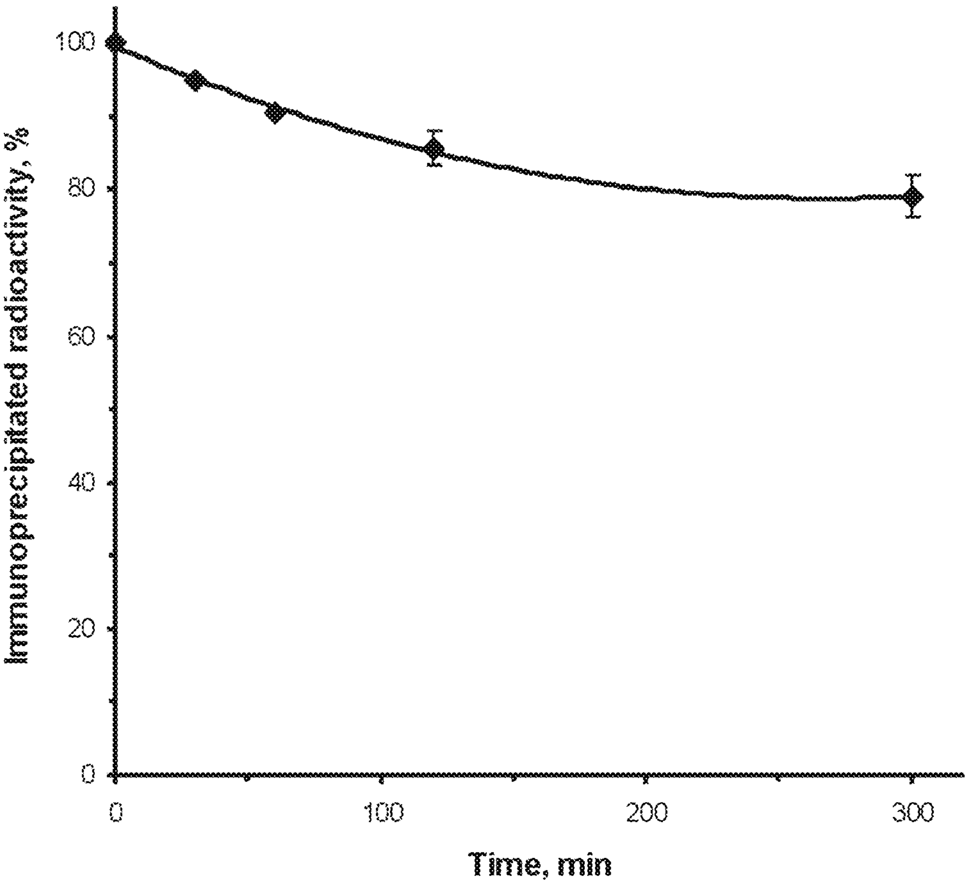

Fig. 8. Immunoprecipitation of ([$^{57}$Co]-protoporphyrin IX)-MTP complexes after incubation in murine blood plasma for indicated time. The rabbit ant-MNT AB was used for the immunoprecipitation analysis according PICRIA (Shersted H.C., Brandst I., Svehag S.-E., and Jensenius J.C. 1981. Quantitation of circulating immune complexes by combined PEG precipitation and immunoglobin-specific radioimmunoassay (PICRIA). In: Methods in Enzymology, 71: 538-550).

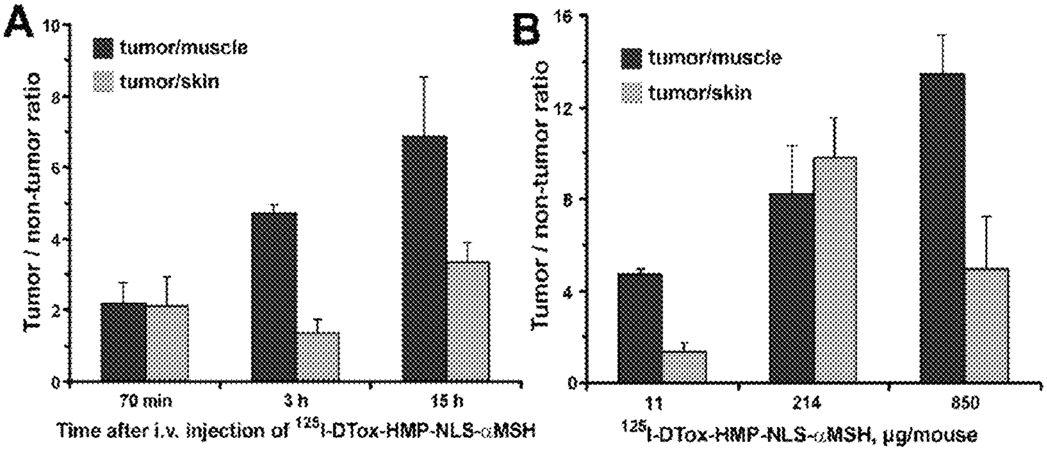
Fig. 9. Tumor-to-tissue ratios of $^{125}I$ after intravenous injection of $^{125}I$-labeled DTox-HMP-NLS- αMSH in B16-F1 melanoma-bearing C57Black/6J mice. (*A*) Effect of time; 11 μg MTP dose. (*B*) Effect of MTP dose; 3 h post injection.

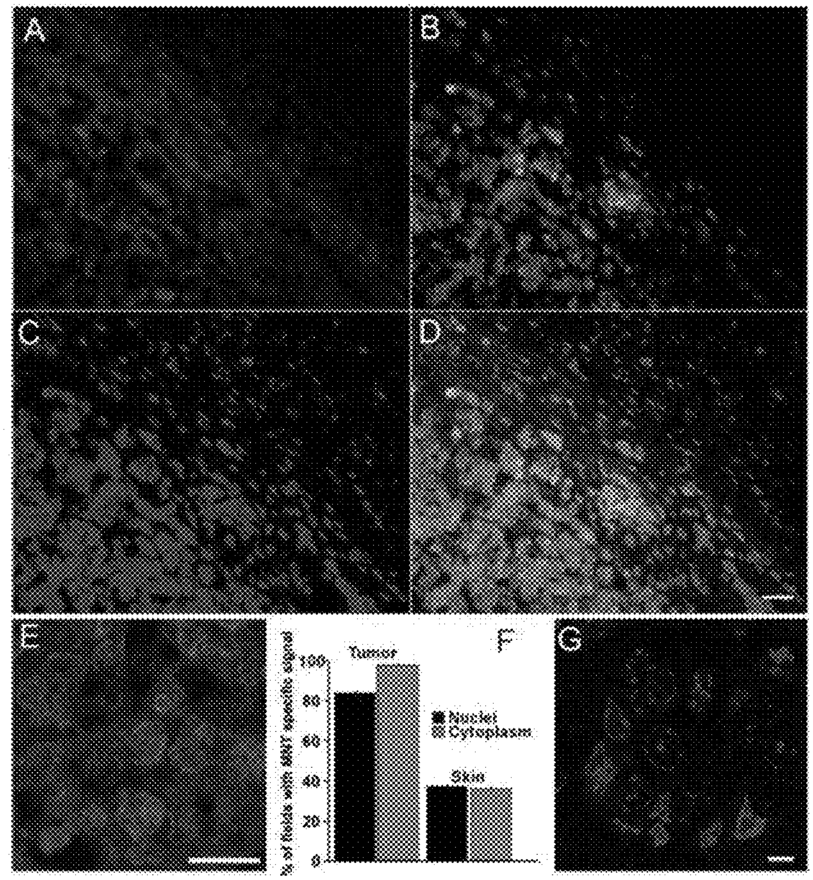

Fig. 10. Immunofluorescence analysis of *in vivo* distribution in tumor and neighboring tissue, and subcellular localization of MTP 3 h after intravenous injection in mice. (*A*)-(*F*) 10 μm tissue sections from DBA/2 mice bearing murine Cloudman melanoma S91 transformed with GFP receiving DTox-HMP-NLS-αMSH. (*A*)-(*D*) tumor and surrounding tissue section (40x). (*A*) Alexa Fluor 555 staining for MTP (red); (*B*) GFP fluorescence from tumor cells (green); (*C*) DAPI staining of cell nuclei (blue); (*D*) overlay of *A*, *B* and *C*. (*E*) tumor section (63x): overlay of DAPI fluorescence (blue) and MTP (red). (*F*) % of fields (± SEM) with specific MTP signal in nuclei and cytoplasm of tumor and neighboring skin cells. (*G*) 2-3 *μ*m tumor section (63x) from Balb/c ByJIco-*nu/nu* mouse bearing human A431 epidermoid carcinoma 3 h after intravenous injection of chlorin $e_6$-DTox-HMP-NLS-EGF; overlay of DAPI fluorescence (blue) and MTP (red). (Scale bars: *D* and *E*, 20 *μ*m; *G*, 5 μm)

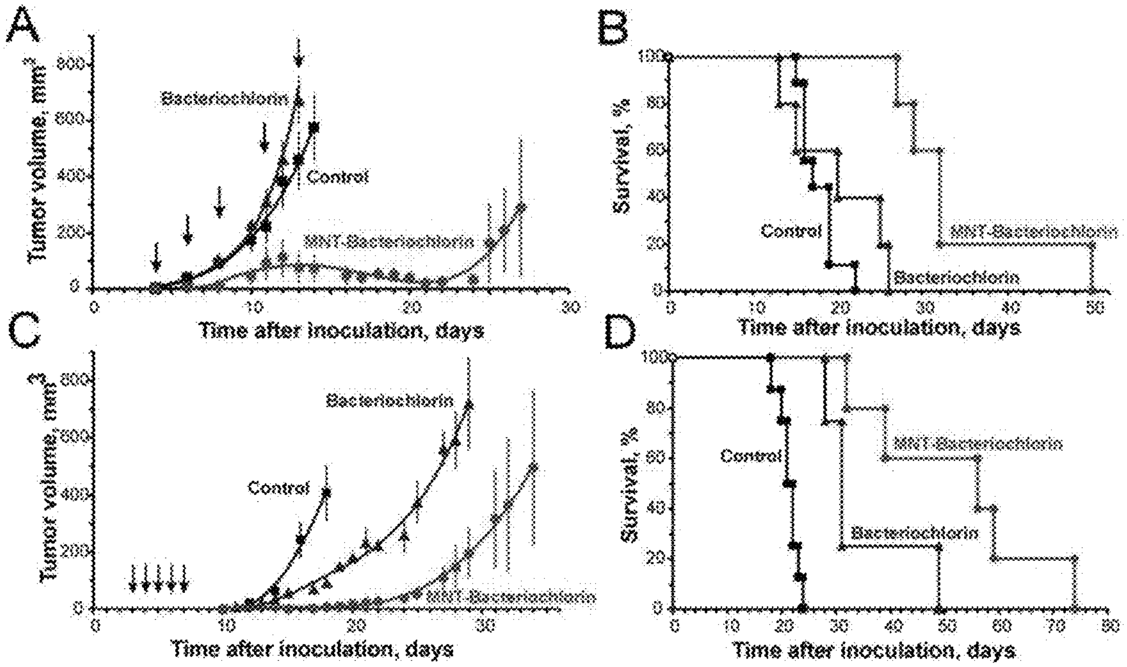

Fig. 11. Comparative efficacy of photodynamic therapy with bacteriochlorin *p* conjugated with DTox-HMP-NLS-αMSH MTP and free bacteriochlorin *p*. (*A*)-(*B*) C57Black/6J mice with subcutaneous B16-F1 murine melanoma; (*A*) tumor growth, mean ± SEM; injection and illumination cycles are indicated with arrows; average tumor volumes are shown up to the last day when all animals were alive in a group. (*B*) Kaplan-Meier survival curves; (*C*)–(*D*) DBA/2 mice with subcutaneous Cloudman S91 murine melanoma; (*C*) tumor growth, mean ± SEM; injection and illumination cycles are indicated with arrows; average tumor volumes are shown up to the last day when all animals were alive in a group. (*D*) Kaplan-Meier survival curves.

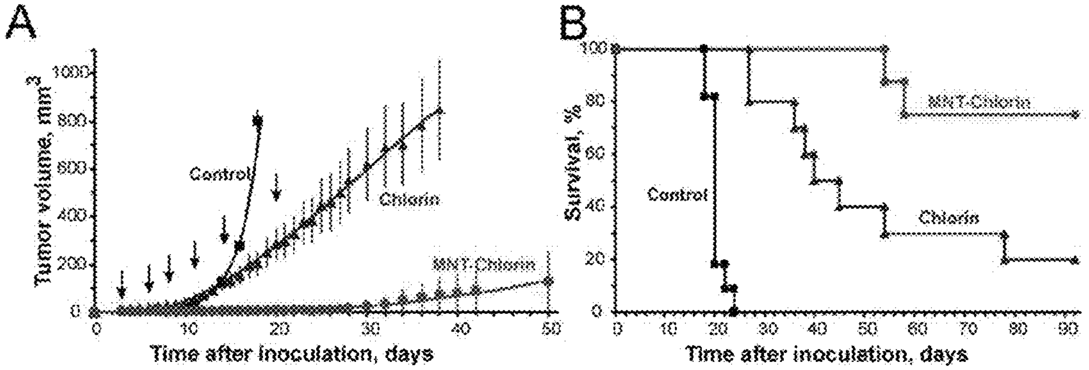

Fig. 12. Photodynamic therapy with chlorin $e_6$ conjugated with DTox-HMP-NLS-EGF MTP inhibits A431 human epidermoid carcinoma growth and enhances survival of tumor-bearing Balb/c ByJIco-*nu/nu* mice compared with free chlorin $e_6$. (*A*) A431 tumor growth, mean ± SEM; injection and illumination cycles are indicated with arrows; average tumor volumes are shown up to the last day when all animals were alive in a group. (*B*) Kaplan-Meier survival curves.

MODULAR TRANSPORT PLATFORM FOR TARGETED DELIVERY OF THERAPEUTIC AGENTS

CROSS-REFERENCE TO RELATED APPLICATIONS

This application claims priority to provisional patent application No. 61/489,181, filed on May 23, 2011, and provisional patent application No. 61/528,971 filed on Aug. 30, 2011, the contents of both of which are incorporated herein in their entirety by reference.

TECHNICAL FIELD

The field of the invention generally relates to the targeted delivery of therapeutic agents for treatment of medical conditions by using a modular transport platform with multiple modules for controlling the delivery of the therapeutic agent. The field of the invention also relates to the targeted delivery of distinct agents for diagnosing medical conditions or for research purposes.

BACKGROUND

A major problem in the treatment of cancer and some other conditions is poor or of negligible efficiency of the specific targeting of drugs to the diseased abnormal cells and not to other unaffected cells. Ideally, such a drug should act over short distances to minimize damage to healthy cells and target subcellular compartments that have the highest sensitivity to the drug. Many pharmaceuticals bind to cell surface receptors and reveal their action via receptor-induced processes. Pharmaceutical agents, however, often do not localize directly within the subcellular compartments of the cell which are the key sites of their action, however, meaning that the most potent action of the drug may not be achieved.

One method to target subcellular compartments that is in development attempts to target the nucleus of the cell. For example, Dinara G. Gilyazova et al. [Targeting Cancer Cells by Novel Engineered Modular Transporters, Cancer Res. 2006; 66:(21): 10534-10540], describe modular recombinant transporters that target photosensitizers to the nucleus, where their action is most pronounced, of cancer cells overexpressing ErbB1 receptors. The described transporters consist of (a) epidermal growth factor as the internalizable ligand module to ErbB1 receptors, (b) the optimized nuclear localization sequence of SV40 large T-antigen, (c) a translocation domain of diphtheria toxin as an endosomolytic module, and (d) the *Escherichia coli* hemoglobin-like protein HMP as a carrier module.

U.S. Pat. No. 6,500,800 [Sobolev et al.] describes a composition for causing photodynamic damage to target cells. The composition includes a photosensitizer, a photosensitizer carrier component, a component which enables target cell recognition and transport of the photosensitizer toward the interior of the target cell by specific receptor-mediated endocytosis, and a component capable of effective targeted transport of the photosensitizer within the target cells. The composition is used to cause photodynamic damage to target cells according to the following steps: adding the composition to the cells; keeping the cells at a temperature of normal vital activity of cells with the composition for causing photodynamic damage to the target cells, the composition including the above components; and exposure of the cells to light.

U.S. Pat. No. 7,655,753 to Deonarain et al. is directed to a polypeptide comprising at least one alpha-helix having synthetically attached thereto a plurality of therapeutic or diagnostic moieties. The therapeutic or diagnostic moieties may be the same or different and are spatially oriented on the polypeptide so as to minimize interactions between the moieties. Further aspects of the '753 patent relate to a pharmaceutical composition comprising the polypeptide; a polynucleotide sequence encoding the polypeptide; an expression vector comprising said polynucleotide sequence; and a host cell transformed with said expression vector. The '753 patent also provides a method of treatment comprising administering to a subject in need thereof a therapeutically effective amount of the polypeptide.

The '753 patent appears to disclose a system that includes an alpha-helix polypeptide to which is attached a plurality of therapeutic or diagnostic moieties. The polypeptide may include two or more alpha-helical polypeptides in the form of a multi-helix bundle. The alpha-helix polypeptide of the '753 patent differs from the MTP disclosed herein in a number of respects. For example, the construct of the '753 patent appears to require assembly non-covalently from several different alpha-helix polypeptides. In contrast, the MTP disclosed herein is a single polypeptide. Further the '753 patent appears to consider only mutant forms of the ROP protein, namely the variant with four alpha-helices where at least one of them may be used for joining of an acting principle.

The '753 patent also appears to disclose the targeting protein and polypeptide being linked directly or indirectly via a linker moiety. With indirect linkage the linker moiety bonds the targeting protein to the fusion protein. Direct linkage may occur through any convenient functional group on one of the proteins, such as a hydroxy, carboxy or amino group. Indirect linkage will occur through a linking moiety. The functional groups on the linker moiety are used to form covalent bonds between the alpha helix and targeting protein.

At col. 9, lines 56-67, the '753 patent explains that the linker moiety is used for a chemical reaction via "bi- and multi-functional alkyl, aryl, aralkyl or peptidic moieties, alkyl, aryl or aralkyl aldehydes acids esters and anyhdrides, sulphydryl or carboxyl groups, such as maleimido benzoic acid derivatives, maleimido proprionic acid derivatives and succinimido derivatives or may be derived from cyanuric bromide or chloride, carbonyldiimidazole, succinimidyl esters or sulphonic halides and the like. The functional groups on the linker moiety used to form covalent bonds between the alpha helix and targeting elements may be two or more of, e.g., amino, hydrazino, hydroxyl, thiol, maleimido, carbonyl, and carboxyl groups, etc. The linker moiety may include a short sequence of from 1 to 4 amino acid residues." Such a linker moiety differs from the use in the instant invention of a spacer between a module and the rest of the MTP of the present invention. In one aspect of the present invention, the spacers (e.g., flexible amino-acid inserts) are used to achieve higher MTP affinity to a receptor.

The polypeptide in the '753 patent further includes a sub-cellular targeting peptide and a membrane active peptide. The sub-cellular targeting peptide may be attached either to the targeting element or to the alpha helix of the polypeptide, or to both. Examples of sub-cellular targeting peptides include nuclear localization sequences (NLS). The additional sequences can also be membrane-active peptides which function to disrupt the endosomal compartment containing the fusion protein after internalization. This will facilitate the release of the therapeutic agent into the cytosol of the cell where it can have a potent action. However, the '753 patent does not disclose a pH dependence of action of the peptides in disrupting the endosomal compartment.

As described herein, the MTP of the instant invention may include a special module which becomes membrane active only under special conditions, namely, in a slightly acidic milieau. For example, the activity of the module may have an activity maxima at pH 5.5. This action of this module is proved experimentally, described below, and has been shown to give a pore formation in lipid bilayers by the MTP of the present application under these conditions. Moreover, it should be understood that the pore formation as well as an endosomal/lysosomal activity at pH 3-pH 6 is a result of combined actions of two MTP modules, namely the endosomolytic module and the carrier module.

In one aspect, the invention described herein may have a necessity of combined action of a carrier module, HMP, and an endosomolytic module in order to make pores in lipid membranes at acidic pH's for subsequent MTP release from endosomes. It also should be added that the MTP can include a special module not only for specific subcellular targeting but also for retaining in the specific subcellular compartment of target cells (i.e., the nuclei of cancer cells).

The '753 patent also describes the therapeutic or diagnostic agent being attached directly to the polypeptide, or by virtue of a linker group. One of the properties of the MTP described herein is its ability to include an agent to be transported non-covalently, into the hydrophobic pocket of the carrier module. As described below, this can be done (i) either directly, into the porphyrin moiety that can be then inserted into the pocket, or (ii) indirectly, i.e. linked to the porphyrin derivative that can be then inserted into the pocket.

Another relevant patent is U.S. Pat. No. 6,821,948 to Braun et al, which relates to conjugates for mediating a cell-specific, compartment-specific or membrane-specific to methods of active substances. The conjugates include: a transport mediator for the cell membrane, a cell-specific, compartment-specific or membrane-specific address protein or peptide, and an active substance to be transported. In contrast to the invention described herein, the '948 patent does not disclose a module with a retention function or a non-covalent attachment of drugs.

U.S. Pat. No. 5,674,977 to Gariepy relates to a branched synthetic peptide conjugate which can be designed to bind to a target cell surface receptor, to penetrate into target cells, and to deliver a diagnostic probe or cytotoxic functionality to a desired site of action. The invention provides a relatively small molecule of flexible design having a branched structure for systematically incorporating a desired number of cytotoxic functions, peptide-based localization signals or diagnostic probes. Gariepy describes his invention as addressing problems associated with protein-based therapeutic or diagnostic agents. In contrast to the MTP of the instant invention, Gariepy's system, does not have a pH-dependent endosomolytic function; a module with a retention function; or a non-covalent attachment of drugs.

U.S. Pat. No. 6,498,233 to Wels et al. relates to a nucleic acid transfer system including a translocation domain of toxins, especially of diphtheria toxin suitable for targeting a nucleic acid, e.g., a gene, to a specific cell, and obtaining expression of the nucleic acid. The nucleic acid transfer system includes a multidomain protein component and a nucleic acid component. Wels also relates to the multidomain protein, a nucleic acid encoding the protein, suitable amplification and expression systems for the nucleic acid, and processes for their preparation and uses. In contrast to the invention described herein, Wels does not disclose a compartment-specific function, a retention function, or a function for transport of nucleic acids. In one aspect of the inventions described herein, the MTPs of the instant application may have an endosomolytic module representing a truncated diphtheria toxin translocation domain. This truncation (202-384 aa) was made to discard the cleavable protease site after 194 amino acid as well as 186 and 201 Cysteins, which subtend the cleavable amino acid loop.

U.S. Pat. No. 5,965,406 to Murphy is directed to a recombinant DNA molecule encoding a hybrid protein comprising a first part, a second part, and a third part. The first part comprises a portion of the binding domain of a cell-binding polypeptide ligand effective to cause said hybrid protein to bind to a cell of an animal. The second part comprises a portion of a translocation domain of naturally occurring protein selected from the group consisting of diphtheria toxin, botulinum neurotoxin, ricin, cholera toxin, LT toxin, C3 toxin, Shiga toxin, Shiga-like toxin, pertussis toxin and tetanus toxin, which translocates said third part across the cytoplasmic membrane into the cytosol of the cell. The third part comprises a polypeptide entity to be introduced into the cell. The third part is non-native with respect to the naturally occurring protein of the second part.

In contrast to the MTP described herein, the '406 patent does not disclose a compartment-specific function, a retention function, or the non-covalent attachment of drugs. Further, the MTPs described herein generally will have at least four modules necessary for targeted intranuclear delivery and, are not restricted to only a concrete translocation domain or a domain from the toxin group. In addition, as described above, the MTPs of the instant application may have an endosomolytic module representing a truncated diphtheria toxin translocation domain.

U.S. Pat. No. 6,022,950 to Murphy, similarly discloses a hybrid molecule comprising a first part, a second part, and a third part connected by covalent bonds. The first part includes a portion of the binding domain of a cell-binding polypeptide ligand effective to cause said hybrid protein to bind to a cell of an animal. The second part comprises a portion of a translocation domain of naturally occurring protein which translocates said third part across the cytoplasmic membrane into the cytosol of the cell. The third part comprises a chemical entity to be introduced into the cell. The first part and third part are non-native with respect to the naturally occurring protein, and further the covalent bond connecting the second part and the third part is a cleavable bond. When the second part comprises a portion of a translocation domain of *Pseudomonas* exotoxin, the third part is not a polypeptide. The description notes that MSH can selectively bind to melanocytes, rendering hybrids, once labelled with a detectable label, useful in the diagnosis of melanoma and the in vivo and in vitro detection of metastic melanoma loci. Such a hybrid, when attached to an enzymatically-active portion of a toxin molecule instead of to a detectable label, could be utilized to deliver that toxic activity specifically to the target melanoma cells In contrast to the MTP described herein, the '950 patent does not disclose a retention function, the non-covalent attachment of drugs or any modules/functions for translocation across the cytoplasmic membrane into the cytosol of the cell.

SUMMARY

A key aspect of the invention is a modular transport platform that includes several functional modules within one molecule, and is configured to penetrate a target cell, deliver the modular transporting platform into the target cells, provide pH-dependent membrane disruption activity, directed intracellular transport into a target subcellular compartment of the target cell, and ability to couple the active agent within the modular transport platform. The molecule includes a module for a non-covalent coupling of cyclic tetrapyrrol moieties to the modular transport platform; and a module configured to retain the modular transport platform within the target subcellular compartment.

Embodiments of the modular transport platform may include one or more of the following features. For example, the modular transport platform may include one or more of the following modules:

(1) a ligand module to target a specific receptor on the surface of the target cell by providing specific recognition of the target cell;

(2) an endosomolytic module that provides pH-dependent membrane disruption activity within the target cell to disrupt an endocytotic vesicle to release the MTP within the target cell;

(3) an intracellular transport module to cause delivery of the MTP to a particular subcellular compartment, wherein the intracellular transport module delivers the MTP to the subcellular compartment based on one or more cellular transport mechanism;

(4) a module for subcellular recognition, such as recognition of specified intracellular macromolecules;

(5) a carrier module for unifying the modules and coupling the modules with the transported substance; and (6) a therapeutic, diagnostic or research agent as a substance to be transported by the MTP.

The MTP may include a module for a non-covalent coupling of cyclic tetrapyrrol molecules. The module for non-covalent coupling may have a hydrophobic pocket. The module with the hydrophobic pocket is an *E. coli* hemoglobin-like protein, HMP. The substance to be transported may be coupled to the modular transport platform via the hydrophobic pocket. The substance to be transported may be coupled to the modular transport platform via inserting the substance into the hydrophobic pocket. The substance to be transported may be coupled to the modular transport platform via linkage to a tetrapyrrol molecule inserted non-covalently into the hydrophobic pocket. These tetrapyrrol molecules can be used for non-covalent attachment of drugs. The substance to be transported may be coupled to the modular transport platform via coupling to the tetrapyrrol molecule inserted into hydrophobic pocket.

The substance to be transported may be a radionuclide.

The MTP may be bacterially synthesized as a whole molecule.

The modular transport platform may include a domain for addition of one or modules, said domain comprising intein with or without chitin-binding domain (CBD).

The modular transport platform may be bacterially synthesized as several separated components and then these components integrated to form the MTP. The separated components may be combined via intein. A ligand module can be used as one of the components.

The ligand module that confers penetration of the modular transport platform into a target cell may be bacterially synthesized. The ligand module accomplishing penetration of the modular transport platform into a target cell may be chemically synthesized.

The module with the function of intracellular retention of the modular transport platform within the subcellular compartment of the target cell may interact with specific structures or molecules within the subcellular compartment. The module with the function of intracellular retention of the modular transport platform within the subcellular compartment of the target cell may interact with specific structures or molecules within the cell nucleus. The module with the function of intracellular retention of the modular transport platform within the subcellular compartment of the target cell may interact with DNA. The module with the function of intracellular retention of the modular transport platform within the subcellular compartment of the target cell may interacts with specific structures or molecules within the hyaloplasm. The module with the function of intracellular retention of the modular transport platform within the subcellular compartment of the target cell may interact with proteasomes.

The acting substance to be transported may be attached to the modular transport platform covalently. The acting substance to be transported maybe a radionuclide or a photosensitizer.

A further aspect of the invention is that the entire modular transport platform may be encoded by a plasmid as a single multimodular fusion protein, wherein the modular transport platform confers penetration of said modular transport platform into target cells of choice, pH-dependent membrane disruption activity within the target cells, directed intracellular transport into the cell parts of choice within the target cells, and addition of the acting substance to be transported. The molecule possesses a module for a non-covalent coupling of cyclic tetrapyrrol molecules and a module with a function of intracellular retention of said modular transport platform within an intracellular part of choice. The modular transport platform includes the following modules:

(1) a ligand module to target a specific receptor on the surface of the target cell by providing specific recognition of the target cell;

(2) an endosomolytic module that provides pH-dependent membrane disruption activity within the target cell to disrupt an endocytotic vesicle to release the MTP within the target cell;

(3) an intracellular transport module to cause delivery of the MTP to a particular subcellular compartment, wherein the intracellular transport module delivers the MTP to the subcellular compartment based on one or more cellular transport mechanism;

(4) a module for intracellular retention to ensure retention of the MTP within the subcellular compartment of the target cell;

(5) a module for subcellular recognition, such as recognition of specified intracellular macromolecules;

(6) a therapeutic, diagnostic or research agent as a substance to be transported by the MTP; and (7) a carrier module for unifying the modules and coupling the modules with the transported substance.

Embodiments of the plasmid encoding the modular transport platform may include one or more of the following features or those described above.

In another general aspect, there is provided a method of delivering a therapeutic, diagnostic or research agent as a substance to be transported a modular transport platform. The modular transport platform includes functional modules within one molecule which accomplishes:

penetration of said modular transport platform into target cells;

pH-dependent membrane disruption activity within the target cells to release the modular transport platform;

directed intracellular transport into a targeted intracellular compartment;

addition of the substance to be transported to a module for a non-covalent coupling of cyclic tetrapyrrol molecules; and a module with a function of retention of said modular transport platform within the intracellular compartment of the target cell. The method includes a systemic infusion of the modular transport platform with the substance to be transported attached to the modular transport platform.

In another general aspect there is provided a method of drying, storage and reconstitution of the modular transport platform, such as the MTP described above. The method includes using a buffer to obtain a functional modular transport platform after freeze-drying.

The details of various embodiments of the invention are set forth in the accompanying drawings and the description below. Other features and advantages of the invention will be apparent from the description, the drawings, and the claims.

DESCRIPTION OF THE DRAWINGS

FIG. 1 is a graph showing the effect of MTP posttranslational treatment on affinity of its ligand module to cell receptor.

FIGS. 2A and 2B are schematics illustrating construction of an MTP-encoding plasmid possessing intein and CBD (chitin-binding domain)-encoding regions, purification of the "blank" MTP by affinity chromatography on chitin (Step 1, binding with chitin and Step 2, release of "blank" or non-liganded MTP by a sulfhydryl-containing compound), and the ligand loading step of the non-liganded MTP to the polypeptide ligand (the specific covalent attachment of a ligand with N-terminal cysteine to the "blank" MTP).

FIG. 3 is a gel-shift assay with MTP containing apoptin fragment, DTox-HMP-apo-EGF, and lacking it, DTox-HMP-NLS-EGF. DS-DNA (190 bp) was incubated for 30 min at room temperature with MTPs in 20 mM HEPES buffer, pH 7.4, 10 mM NaCl, 1 mM EDTA; gel-shift assay was accomplished in 2% agarose gel with ethidium bromide staining.

FIG. 4 is graph showing the interaction of DTox-HMP-apo-EGF (left graph) and DTox-HMP-NLS-EGF (right graph) with plasmid DNA as assayed using surface plasmon resonance method, with binding affinity constants shown in the table below.

FIG. 5 is a graph showing the solubility of MTP at different pH conditions.

FIG. 6 is an illustration showing the process for assembling the plasmid encoding the EGF-containing MTP.

FIGS. 7A-C graphically illustrate the insertion of chlorin derivative azidopolyethylene glycol derivative of Co-chlorin complex (FIG. 7A) into the MTP with FIG. 7B illustrating the absorption spectra of the derivative Co-Ch1-PEG-$N_3$ (the optical density of solution in Soret band—0.24) fraction on MRT concentration calculated from MTP-Co-Ch1-PEG-$N_3$ spectra by nonlinear regression from Soret bands of complexes at different MTP concentrations. FIG. 7C illustrates the MTP concentration dependence of binding of Co-Ch1-PEG-$N_3$ to the MTP FIG. 8 demonstrates stability of MTP—porphyrin complex in blood plasma.

FIG. 9 is a pair of graphs showing tumor-to-tissue ratios of $^{125}$I after intravenous injection of $^{125}$I-labeled DTox-HMP-NLS-αMSH in B16-F1 melanoma-bearing C57Black/6J mice with A showing time dependence post-injection (11 μg MTP) and B showing dose dependence (3 h post injection).

FIG. 10 is a series of panels showing results for localization by immunofluorescence/microscopic imaging in vivo in tumor and neighboring tissue 3 h after intravenous injection DTox-HMP-NLS-αMSH and DTox-HMP-NLS-EGF MTP in mice.

FIG. 11 reports the comparative efficacy of photodynamic therapy with bacteriochlorin p conjugated with DTox-HMP-NLS-αMSH MTP and free bacteriochlorin p.

FIG. 12 reports the results of photodynamic therapy using chlorin $e_6$ conjugated to DTox-HMP-NLS-EGF MTP to inhibit A431 human epidermoid carcinoma growth and enhance survival of tumor-bearing Balb/c ByJIco-nu/nu mice compared with free chlorin $e_6$.

DETAILED DESCRIPTION

Figure 2A:
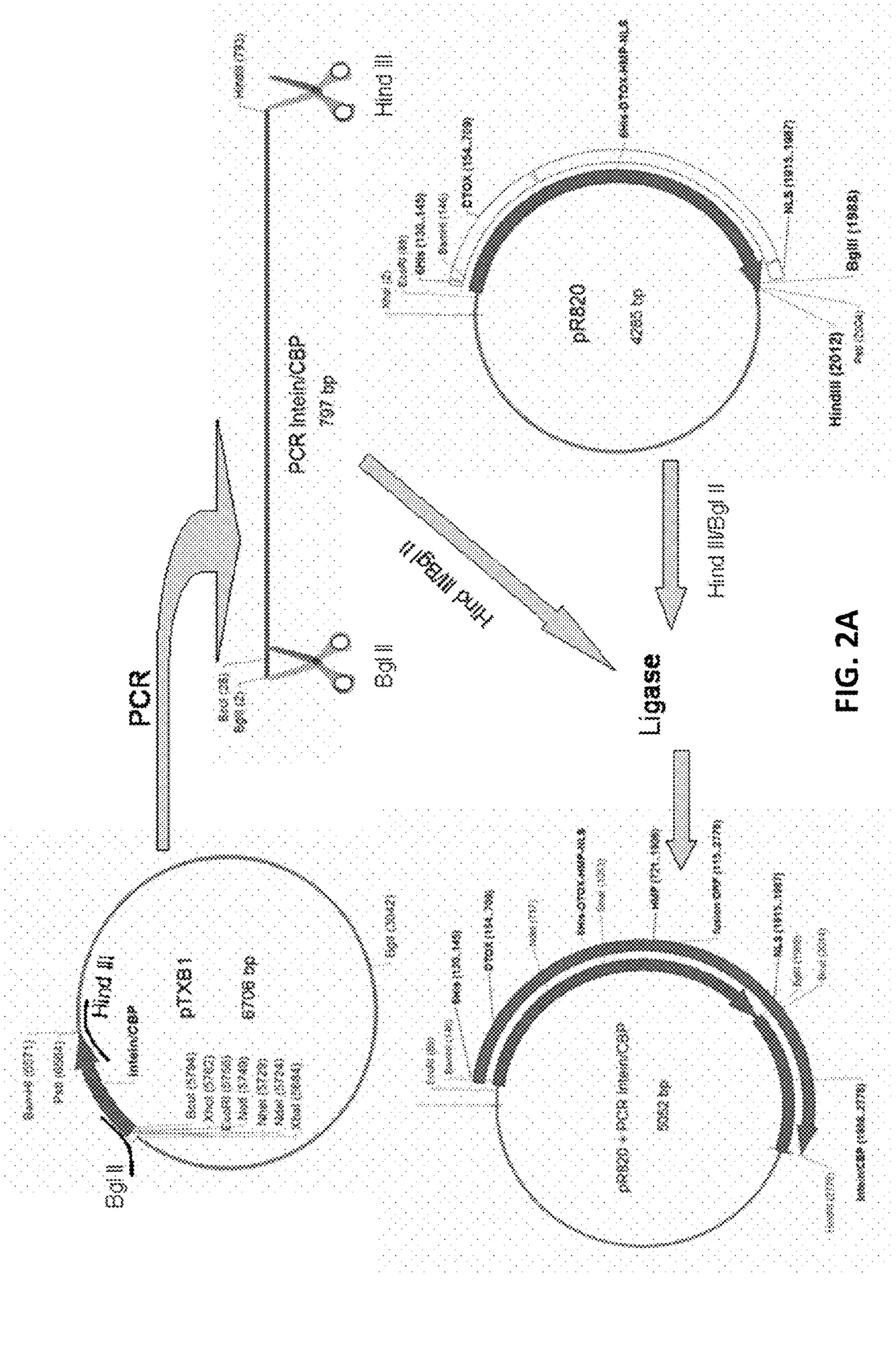

Past research has shown that it is possible to generate a transporter that can deliver a therapeutic agent to specific internalizable receptors on a target cell, can be internalized into the cell via receptor-mediated endocytosis, can escape from endosomes, and can target to a specific organelle or subcellular compartment within the cell. However, there remains the problems of how to couple the therapeutic agent simply and efficiently to the transporter and how to ensure the therapeutic is retained within the targeted organelle. The inventors believe the present invention is the first to accomplish both of these needs efficiently and effectively. Specifically, the inventor has developed a modular transport platform (MTP) which is a new platform with a wide application in delivering therapeutic agents to a specific cell, i.e., the target cell, and optionally to a specific organelle within a cell. In general, the MTP consists of several functional modules that together target the MTP to particular compartments of a targeted cell and cause the therapeutic agent to reach those compartments. The MTP includes one or more of the following modules or components: (1) a ligand module to target a specific receptor on the cell surface thereby providing specific recognition of a target cell; (2) an endosomolytic module that disrupts the endocytotic vesicle to release the MTP within the cell; (3) an intracellular transport module to cause delivery of the MTP to a particular subcellular compartment relying on cellular transport mechanisms; (4) a module for intracellular retention to ensure retention of the MTP within a specific subcellular compartment of the target cell but not in the non-target cells; (5) a module for subcellular recognition, such as recognition of specified intracellular macromolecules; (6) a carrier module for unifying the modules and coupling the modules with the transported substance while providing optimal spatial distribution of the other MTP modules; and (7) a therapeutic, diagnostic or research agent.

For example, if the therapeutic agent to be delivered is very potent or toxic, the MTP approach will be highly beneficial to the patient seeing as the potent/toxic therapeutic agent will be delivered primarily or solely to the target cell by targeting receptors only expressed on the desired target cells, thereby avoiding collateral damage to other non-targeted cells. Similarly, if the target cell over-expresses a particular receptor that is only sparsely expressed in other cells, delivering the MTP to those receptors will primarily deliver the therapeutic agent to the target cells with minimal collateral damage to other non-targeted cells which have the particular receptor. As can therefore be understood, the specificity by which the MTP approach functions will be greatly enhanced when the receptors to which the MTP has an affinity are overexpressed on a targeted cell.

The MTP possesses a unique set of properties which significantly distinguishes the MTP from known drug delivery vehicles such as antibodies, nanoparticles, liposomes, etc. The following listing provides some properties of the MTP, one or more of which may be present in MTP's according to the invention: 1) delivery of a wide spectrum of substances which can be linked to the MTP either covalently or non-covalently; 2) low toxicity (shown in mice); 3) low immunogenicity (according to a delayed hypersensitivity test on mice); 4) a significant, 20 to 3,000 or more times, enhancement of in vitro efficacy of medicines; 5) a significant enhancement of therapeutic efficacy of medicines in vivo (shown in mice); 6) a high level of MTP bacterial production (up to 30% of total soluble protein); 7) simple purification; 8) the possibility to replace MTP modules if one needs to change a type of target cells; 9) biodegradability; 10) inexpensive production; 11) the possibility to freeze-dry the MTP, keep it at room temperature and to reconstruct it without loss of activity; and 12) a long shelf-life.

The MTP also includes the characteristic that it is made of a single polypeptide rather than two or more polypeptides. This offers the following advantage over a product that includes two or more polypeptides. First, because covalent bonds are more stable than non-covalent ones [see e.g. J. M. Goddard, J. H. Hotchkiss. Polymer surface modification for the attachment of bioactive compounds. Prog. Polym. Sci. 2007, 32: 698-725], the MTP should be stable under a wider range of conditions than a non-covalent complex that includes two or more polypeptides. Second, when MTP is synthesized in one step, its production is always more simple than manufacturing two or more polypeptide-containing complexes by 2 or more times. It should be understood, however, that in alternative implementations the MTP can be made of multiple polypeptides.

In general, the MTP will have at least four modules to ensure that the MTP can provide targeted intranuclear delivery of the therapeutic, diagnostic or research agent.

As used herein, a modular transport platform (MTP) is a modular composition with multilevel specificity for delivery of pharmaceutical agents and other substances (hereafter—“substances”) into target cells and once within the target cells—into a predetermined/given subcellular compartment. The MTP exploits intermolecular “recognition” processes as well as intracellular transport processes such as receptor-mediated endocytosis, nucleocytoplasmic transport and others, for instance, transport into mitochondria, Golgi apparatus, peroxisomes, etc.

As may occur herein, any reference to databases, web pages, articles, books and the like are used to provide support for various aspects related to the invention. Because the entire content of the reference or the specific passages of relevance is not included explicitly as text within this application merely for the sake of space, the inventors rely upon incorporating by reference the relevant passages from these documents, databases and web pages. Therefore, the inventors hereby make clear that all databases, web pages, articles, books and the like referenced herein are incorporated in their entirety in this application by reference for the disclosure for which they are referenced.

In general, the process of designing a MTP is according to the following steps:

1. Selection of Pathologies to be Targeted

MTP design is based on determining which treatments benefit from a targeted delivery of therapeutic substances to defined subcellular compartments of target cells. For example, if the treatment does not show a benefit in targeted delivery to defined subcellular compartments of target cells, the MTP may offer fewer advantages compared to less complex delivery systems. The MTP will be advantageous if an overexpressed receptor on the target cell is specific to the target cell. Thus, the MTP can be used in oncology applications, such as head-and-neck cancer, esophageal cancer, glioblastoma, bladder cancer, etc. (for a more complete listing of receptors, see below the “List of surface cell receptors, which genes contain mutations linked to tumor formation”). The MTP also can be applied in cardiology, e.g., ablation of atherosclerotic plaques; viral diseases (e.g., elimination of host cells, inhibition of virion synthesis, e.g., for HIV treatment); gynecology (e.g., endometriosis), to name but a few potential medicinal applications. One of skill in the art can determine which conditions are suitable to treatment by application of the MTP based on a literature review of conditions that involve a particular cell. Suitable databases for searching include medscape.gov, pubmed.gov and other searchable medical databases known to one of skill in the art. For example, if the targeted condition is lupus, the researcher can go to pubmed.gov and search the Medline database using terms such as “lupus target cells.” The researcher can even search the Internet using known search engines such as scholar.google.com. With these search results, the researcher can read through the journal articles reporting cells that are known to be correlated with lupus.

In another embodiment, the MTP can include a ligand module specific for receptors such as: melanocortin receptor-1 (e.g. melanoma), somatostatin receptor (e.g. medulloblastoma), IL3 receptor (e.g. acute myeloid leukemia); MTP carrying internalizable antibodies against Her2/neu and Her3 (e.g. breast cancer). Therefore, because these pathologies have internalizable receptors that can be targeted, these pathologies can be treated using the MTP system described herein. It should be understood that the above listing of receptors is not exhaustive and internalizable receptors, in general, are suitable for targeting by the MTP.

2. Identification of Internalizable Receptors

The second step of the process involves selecting internalizable receptors, which can undergo receptor-mediated endocytosis. As explained in more detail below, the MTP must be internalized within the cell to be effective. Internalization of the MTP is accomplished by binding the MTP to an internalizable receptor. Once bound to the internalizable receptor, an endosome is formed containing the MTP, carrying the MTP inside the cell through receptor-mediated endocytosis. Certain receptors are internalized or sequestered while others are not. By conducting a literature search, one of skill in the art can distinguish between which receptors are internalized and those that are not. For example, if one of skill in the art was to have found a target cell for treating lupus, the researcher would similarly conduct a literature search for the receptors associated with those cells and which cells are internalized. With this understanding, the internalizable receptor should be selected.

For example, considering only cancer and associated tumors, currently numerous receptors are known whose expression can increase dramatically during tumor formation. The following listing provide some of these known receptors.

List of Surface Cell Receptors, which Genes Contain Mutations Linked to Tumor Formation List of surface cell receptors, which genes contain mutations linked to tumor formation*

| Abbreviation/synonym | Tumor type | Identificator** |
|---|---|---|
| ALK (anaplastic lymphoma kinase (Ki-1)) | anaplastic lymphoma | Q9UM73 |
| BMPR1A (bone morphogenetic protein receptor, type IA) | Gastrointestinal tract polipus | P36894 |
| EGFR (epidermal growth factor receptor)/v-erb-b (erythroblastic leukemia viral oncogene homolog, avian) | glioma, non-small cell lung cancer; | P00533 |

-continued

List of surface cell receptors, which genes contain mutations linked to tumor formation*

| Abbreviation/synonym | Tumor type | Identi-ficator** |
|---|---|---|
| ERBB2 (v-erb-b2, erythroblastic leukemia viral oncogene homolog 2, neuro/glioblastoma derived oncogene homolog (avian) | Breast cancer, ovarian cancer and many others | P04626 |
| FGFR1 (fibroblast growth factor receptor 1) | myeloproliferative diseases, non-Hodgkin lymphoma | P11362 |
| FGFR2 (fibroblast growth factor receptor 2) | Gastric cancer | P21802 |
| FGFR3 (fibroblast growth factor receptor 3) | Bladder cancer, multiple myeloma | P22607 |
| FLT3 (fms-related tyrosine kinase) | Acute myelogenic leukosis, acute myeloblastic leukemia | P36888 |
| FLT4/VEGFR3/VPF (fms-related tyrosine kinase/vascular endothelin growth factor/vascular permeability factor receptor) | angiosarcoma | P35916 |
| IL21R (interleukin 21 receptor) | Non-Hodgkin lymphoma | Q9HBE5 |
| IRTA1 (immunoglobulin superfamily receptor translocation associated 1) | B-cell non-Hodgkin lymphoma | NP_112572 |
| c-KIT (v-kit Hardy-Zuckerman 4 feline sarcoma viral oncogene homolog)/stem-cell receptor | stromal intestinal tumors; acute myelo-leukosis, seminoma, mastocytosis, epithelioma | P10721 |
| MET (met proto-oncogene)/ hepatocyte growth factor receptor | Renal papilloma, squamous cell head and neck cancer | P08581 |
| NTRK1 (neurotrophic tyrosine kinase, receptor, type 1) | Thyroid cancer | P04629 |
| NTRK3 (neurotrophic tyrosine kinase, receptor, type 3) | Congenital fibro-sarcoma, breast cancer | Q16288 |
| PDGFRA platelet-derived growth factor, alpha-receptor | stromal intestinal tumors, idiopathic hyperthyroidism, | P16234 |
| PDGFRB (platelet-derived growth factor receptor, beta polypeptide) | acute myeloid leu-kemia, chronic myeloid leukemia, chronic my-elomonocytic leukemia myeloproliferative disorders | NP_002600 |
| RARA (retinoic acid receptor, alpha) | acute promyelocytic leukemia, | P10276 |
| RET (ret proto-oncogene) | thyroid tumours, pheochromocytoma | P07949 |
| TEK/TIE2 | Extraskeletal myxoid chondrosarcoma | P42680 |
| TFRC (transferrin receptor)/p90/ CD71 | Non-Hodgkin lymphoma | P02786 |
| TNFRSF6 (tumor necrosis factor receptor superfamily, member 6)/FAS | testicular germinal cells tumours, NK-T-call lymphoma, squamous cell skin neoplasias, | P25445 |
| TSHR (thyroid stimulating hormone receptor) | toxic thyroid adenoma | P16473 |
| VEGFR | Breast cancer, renal cell carcinoma, and many other types of cancer | P35968 |

*based on data collected and updated by Sanger (The Wellcome Trust Sanger Institute), Cambridge, UK (sanger.ac.uk/genetics/CGP/Census/).
**standard international protein identificator (Swissprot/Refseq).

Increased expression of corresponding protein products was shown for the majority of genes mentioned above-EGFR [Bacus et al., 1990; Gillaspy et al., 1992; Rikimaru et al., 1992; Ching et al., 1993; Untawale et al., 1993; Hoi et al., 1995; Chen et al., 1999; Huang and Harari, 1999; Azemar et al., 2000; Charoenrat et al., 2000; Nouri et al., 2000; Charoen-rat et al., 2001; Halatsch et al., 2001; Udart et al., 2001; Ono et al., 2002; Earp, III et al., 2003; Ford and Grandis, 2003; Jungbluth et al., 2003; Kanematsu et al., 2003; Ritter and Arteaga, 2003], ErbB2 for example the reviews [Cirisano and Karlan, 1996; Kumar and Yarmand-Bagheri, 2001; Wang et al., 2001], fibroblast growth factor receptor [Jacquemier et al., 1994; McLeskey et al., 1994; Morrison et al., 1994; Giri et al., 1999; Pollett et al., 2002], hepatocytes growth factor receptot/met-protooncogene [Liu et al., 1998; Porte et al., 1998], nerve growth factor receptor [Walch et al., 1999], transferrin receptor [Hogemann-Savellano et al., 2003].

Quite often the elevated expression of growth factor receptors correlates with the unfavorable forecast of disease progression, with increased invasiveness and metastatic abilities. [Chrysogelos et al., 1994; Ito et al., 1997; Xu et al., 1997; Ciardiello and Tortora, 1998; Dunn et al., 1998; Hsieh et al., 1998; Kwong and Hung, 1998; Charoenrat et al., 2000; Chen et al., 2001; Hernan et al., 2003; Khalil et al., 2003; Baxevanis et al., 2004].

Apart from surface proteins where mutations are causally linked to cancer itself, a number of other surface proteins exist on tumor cells that are overexpressed in comparison with normal cells due to intracellular changes in biochemical processes when malformation occurs. They are: insulin receptors—hepatoma, breast cancer [Frittitta et al., 1997; Pandini et al., 1999; Finlayson et al., 2003; Scharf and Braulke, 2003; Alexia et al., 2004], insulin like growth factor 1—different carcinomas and osteosarcomas, thyroid tumors [Weiner, 1995; Xie et al., 1999; Pandini et al., 1999; Yu and Rohan, 2000; Khandwala et al., 2000; Vella et al., 2001; Ouban et al., 2003; Sekharam et al., 2003; Gydee et al., 2004; Gharib et al., 2004], somatostatin—neuroendocrine tumors [de Jong et al., 2002; Kwekkeboom and Krenning, 2002; de Herder et al., 2004], α-melanocyte stimulating hormone—melanoma [Jiang et al., 1996; Funasaka et al., 1999; Loir et al., 1999; Wikberg et al., 2000], low density lipoproteins—lymphoma, carcinoma [Vitols et al., 1996; Tatidis et al., 2002], macrophage stimulating protein (macrophage dispersion factor)—breast cancer [Maggiora et al., 1998; Peace et al., 2001], folate—brain and ovarian tumors [Weitman et al., 1992; Mantovani et al., 1994], and others as known to one of skill in the art.

It is worth mentioning that elevated protein expression in tumors is not necessarily linked to gene amplification. A number of examples exist of: increase in oncogenes' expression without gene amplification [Chaffanet et al., 1992; Kolibaba and Druker, 1997a; Perez et al., 2002; Nakamura et al., 2003; Mueller et al., 2004; Kersting et al., 2004; Mrhalova et al., 2005; Saxby et al., 2005], and increase in number of gene copies, without elevated levels of expression. [Dawkins et al., 1993; Kolibaba and Druker, 1997b; Durbecq et al., 2004].

The articles referenced to above are incorporated herein as representing receptors selected as suitable for targeting:

1. Alexia C., Fallot G., Lasfer M., Schweizer-Groyer G., and Groyer A. An evaluation of the role of insulin-like growth factors (IGF) and of type-I IGF receptor signalling in hepatocarcinogenesis and in the resistance of hepatocarcinoma cells against drug-induced apoptosis//Biochem Pharmacol-2004.-V. 68.-P. 1003-1015.
2. Azemar M., Schmidt M., Arlt F., Kennel P., Brandt B., Papadimitriou A., Groner B., and Wels W. Recombinant antibody toxins specific for ErbB2 and EGF receptor inhibit the in vitro growth of human head and neck cancer cells and cause rapid tumor regression in vivo//Int. J. Cancer-2000.-V. 86.-P. 269-275.
3. Bacus S. S., Ruby S. G., Weinberg D. S., Chin D., Ortiz R., and Bacus J. W. HER-2/neu oncogene expression and proliferation in breast cancers//Am. J. Pathol.-1990.-V. 137.-P. 103-111.

4. Baxevanis C. N., Sotiropoulou P. A., Sotiriadou N. N., and Papamichail M. Immunobiology of HER-2/neu oncoprotein and its potential application in cancer immunotherapy//Cancer Immunol. Immunother.-2004.-V. 53.-P. 166-175.
5. Chaffanet M., Chauvin C., Laine M., Berger F., Chedin M., Rost N., Nissou M. F., and Benabid A. L. EGF receptor amplification and expression in human brain tumours//Eur. J. Cancer-1992.-V. 28.-P. 11-17.
6. Charoenrat P., Rhys-Evans P., and Eccles S. Characterization of ten newly-derived human head and neck squamous carcinoma cell lines with special reference to c-erbB proto-oncogene expression//Anticancer Res.-2001.-V. 21.-P. 1953-1963.
7. Charoenrat P., Rhys-Evans P., Modjtahedi H., Court W., Box G., and Eccles S. Overexpression of epidermal growth factor receptor in human head and neck squamous carcinoma cell lines correlates with matrix metalloproteinase-9 expression and in vitro invasion//Int. J. Cancer-2000.-V. 86.-P. 307-317.
8. Chen B. K., Ohtsuki Y., Furihata M., Takeuchi T., Iwata J., Liang S. B., and Sonobe H. Co-overexpression of p53 protein and epidermal growth factor receptor in human papillary thyroid carcinomas correlated with lymph node metastasis, tumor size and clinicopathologic stage//Int. J. Oncol.-1999.-V. 15.-P. 893-898.
9. Chen Y., Emtage P., Zhu Q., Foley R., Muller W., Hitt M., Gauldie J., and Wan Y. Induction of ErbB-2/neu-specific protective and therapeutic antitumor immunity using genetically modified dendritic cells: enhanced efficacy by cotransduction of gene encoding IL-12//Gene Ther.-2001.-V. 8.-P. 316-323.
10. Ching K. Z., Ramsey E., Pettigrew N., D'Cunha R., Jason M., and Dodd J. G. Expression of mRNA for epidermal growth factor, transforming growth factor-alpha and their receptor in human prostate tissue and cell lines//Mol. Cell. Biochem.-1993.-V. 126.-P. 151-158.
11. Chrysogelos S. A., Yarden R. I., Lauber A. H., and Murphy J. M. Mechanisms of EGF receptor regulation in breast cancer cells//Breast Cancer Res. Treat.-1994.-V. 31.-P. 227-236.
12. Ciardiello F. and Tortora G. Interactions between the epidermal growth factor receptor and type I protein kinase A: biological significance and therapeutic implications//Clin. Cancer Res.-1998.-V. 4.-P. 821-828.
13. Cirisano F. D. and Karlan B. Y. The role of the HER-2/neu oncogene in gynecologic cancers//J Soc. Gynecol. Investig.-1996.-V. 3.-P. 99-105.
14. Dawkins H. J., Robbins P. D., Sarna M., Carrello S., Harvey J. M., and Sterrett G. F. c-erbB-2 amplification and overexpression in breast cancer: evaluation and comparison of Southern blot, slot blot, ELISA and immunohistochemistry//Pathology-1993.-V. 25.-P. 124-132.
15. de Herder W. W., Krenning E. P., Van Eijck C. H., and Lamberts S. W. Considerations concerning a tailored, individualized therapeutic management of patients with (neuro)endocrine tumours of the gastrointestinal tract and pancreas//2004.—V. 11.—
16. de Jong M., Valkema R., Jamar F., Kvols L. K., Kwekkeboom D. J., Breeman W. A., Bakker W. H., Smith C., Pauwels S., and Krenning E. P. Somatostatin receptor-targeted radionuclide therapy of tumors: preclinical and clinical findings//Semin. Nucl. Med.-2002.-V. 32.-P. 133-140.
17. Dunn S. E., Ehrlich M., Sharp N. J., Reiss K., Solomon G., Hawkins R., Baserga R., and Barrett J. C. A dominant negative mutant of the insulin-like growth factor-I receptor inhibits the adhesion, invasion, and metastasis of breast cancer//Cancer Res.-1998.-V. 58.-P. 3353-3361.
18. Durbecq V., Desmed C., Paesmans M., Cardoso F., Di Leo A., Mano M., Rouas G., Leroy J. Y., Sotiriou C., Piccart M., and Larsimont D. Correlation between topoisomerase-IIalpha gene amplification and protein expression in HER-2 amplified breast cancer//Int. J. Oncol.-2004.-V. 25.-P. 1473-1479.
19. Earp H. S., III, Calvo B. F., and Sartor C. I. The EGF receptor family—multiple roles in proliferation, differentiation, and neoplasia with an emphasis on HER4//Trans. Am. Clin. Climatol. Assoc.-2003.-V. 114.-P. 315-333.
20. Finlayson C. A., Chappell J., Leitner J. W., Goalstone M. L., Garrity M., Nawaz S., Ciaraldi T. P., and Draznin B. Enhanced insulin signaling via Shc in human breast cancer//Metabolism-2003.-V. 52.-P. 1606-1611.
21. Ford A. C. and Grandis J. R. Targeting epidermal growth factor receptor in head and neck cancer//Head Neck-2003.-V. 25.-P. 67-73.
22. Frittitta L., Cerrato A., Sacco M. G., Weidner N., Goldfine I. D., and Vigneri R. The insulin receptor content is increased in breast cancers initiated by three different oncogenes in transgenic mice//Breast Cancer Res Treat-1997.-V. 45.-P. 141-147.
23. Funasaka Y., Sato H., Chakraborty A. K., Ohashi A., Chrousos G. P., and Ichihashi M. Expression of proopiomelanocortin, corticotropin-releasing hormone (CRH), and CRH receptor in melanoma cells, nevus cells, and normal human melanocytes//J. Investig. Dermatol. Symp. Proc.-1999.-V. 4.-P. 105-109.
24. Gharib T. G., Chen G., Huang C. C., Misek D. E., Iannettoni M. D., Hanash S. M., Orringer M. B., and Beer D. G. Genomic and proteomic analyses of vascular endothelial growth factor and insulin-like growth factor-binding protein 3 in lung adenocarcinomas//Clin Lung Cancer-2004.-V. 5.-P. 307-312.
25. Gillaspy G. E., Mapstone T. B., Samols D., and Goldthwait D. A. Transcriptional patterns of growth factors and proto-oncogenes in human glioblastomas and normal glial cells//Cancer Lett.-1992.-V. 65.-P. 55-60.
26. Giri D., Ropiquet F., and Ittmann M. Alterations in expression of basic fibroblast growth factor (FGF) 2 and its receptor FGFR-1 in human prostate cancer//Clin. Cancer Res.-1999.-V. 5.-P. 1063-1071.
27. Gydee H. A. R. K., O'Neill J. T., Patel A. N. E. E., Bauer A. J., Tuttler R. M., and Francis G. L. Differentiated Thyroid Carcinomas from Children and Adolescents Express IGF-I and the IGF-I Receptor (IGF-1-R). Cancers with the Most Intense IGF-1-R Expression May Be More Aggressive//Pediatr Res-2004.-V. 55.-P. 709-715.
28. Halatsch M. E., Schmidt U., Botefur I. C., Holland J. F., and Ohnuma T. Overexpression of deletion-mutant epidermal growth factor receptor is associated with altered genotoxic stress-provoked p53 mRNA induction in a human glioblastoma cell line//Anticancer Res.-2001.-V. 21.-P. 189-195.
29. Hernan R., Fasheh R., Calabrese C., Frank A. J., Maclean K. H., Allard D., Barraclough R., and Gilbertson R. J. ERBB2 up-regulates S100A4 and several other prometastatic genes in medulloblastoma//Cancer Res.-2003.-V. 63.-P. 140-148.
30. Hogemann-Savellano D., Bos E., Blondet C., Sato F., Abe T., Josephson L., Weissleder R., Gaudet J., Sgroi D., Peters P. J., and Basilion J. P. The transferrin receptor: a potential molecular imaging marker for human cancer//Neoplasia.-2003.-V. 5.-P. 495-506.

31. Hoi S. U., Espiritu O. D., Kelley P. Y., Klauber M. R., and Hatton J. D. The role of the epidermal growth factor receptor in human gliomas: I. The control of cell growth//J. Neurosurg.-1995.-V. 82.-P. 841-846.

32. Hsieh C. C., Chow K. C., Fahn H. J., Tsai C. M., Li W. Y., Huang M. H., and Wang L. S. Prognostic significance of HER-2/neu overexpression in stage I adenocarcinoma of lung//Ann. Thorac. Surg.-1998.-V. 66.-P. 1159-1163.

33. Huang S. M. and Harari P. M. Epidermal growth factor receptor inhibition in cancer therapy: biology, rationale and preliminary clinical results//Invest New Drugs-1999.-V. 17.-P. 259-269.

34. Ito M., Nakashima M., Alipov G. K., Matsuzaki S., Ohtsuru A., Yano H., Yamashita S., and Sekine I. Gastric cancer associated with overexpression of parathyroid hormone-related peptide (PTHrP) and PTH/PTHrP receptor in relation to tumor progression//J Gastroenterol.-1997.-V. 32.-P. 396-400.

35. Jacquemier J., Adelaide J., Parc P., Penault-Llorca F., Planche J., deLapeyriere O., and Birnbaum D. Expression of the FGFR1 gene in human breast-carcinoma cells//Int. J. Cancer-1994.-V. 59.-P. 373-378.

36. Jiang J., Sharma S. D., Fink J. L., Hadley M. E., and Hruby V. J. Melanotropic peptide receptors: membrane markers of human melanoma cells//Exp. Dermatol.-1996.-V. 5.-P. 325-333.

37. Jungbluth A. A., Stockert E., Huang H. J., Collins V. P., Coplan K., Iversen K., Kolb D., Johns T. J., Scott A. M., Gullick W. J., Ritter G., Cohen L., Scanlan M. J., Cavenee W. K., Old L. J., and Cavanee W. K. A monoclonal antibody recognizing human cancers with amplification/overexpression of the human epidermal growth factor receptor//Proc. Natl. Acad. Sci. U.S. A-2003.-V. 100.-P. 639-644.

38. Kanematsu T., Yano S., Uehara H., Bando Y., and Sone S. Phosphorylation, but not overexpression, of epidermal growth factor receptor is associated with poor prognosis of non-small cell lung cancer patients//Oncol. Res.-2003.-V. 13.-P. 289-298.

39. Kersting C., Tidow N., Schmidt H., Liedtke C., Neumann J., Boecker W., van Diest P. J., Brandt B., and Buerger H. Gene dosage PCR and fluorescence in situ hybridization reveal low frequency of egfr amplifications despite protein overexpression in invasive breast carcinoma//Lab Invest-2004.-V. 84.-P. 582-587.

40. Khalil M. Y., Grandis J. R., and Shin D. M. Targeting epidermal growth factor receptor: novel therapeutics in the management of cancer//Expert. Rev. Anticancer Ther.-2003.-V. 3.-P. 367-380.

41. Khandwala H. M., McCutcheon I. E., Flyvbjerg A., and Friend K. E. The Effects of Insulin-Like Growth Factors on Tumorigenesis and Neoplastic Growth//Endocr Rev-2000.-V. 21.-P. 215-244.

42. Kolibaba K. S. and Druker B. J. Protein tyrosine kinases and cancer//Biochim. Biophys. Acta-1997b.-V. 1333.-P. F217-F248.

43. Kolibaba K. S. and Druker B. J. Protein tyrosine kinases and cancer//Biochim. Biophys. Acta-1997a.-V. 1333.-P. F217-F248.

44. Kumar R. and Yarmand-Bagheri R. The role of HER2 in angiogenesis//Semin. Oncol.-2001.-V. 28.-P. 27-32.

45. Kwekkeboom D. J. and Krenning E. P. Somatostatin receptor imaging//Semin. Nucl. Med.-2002.-V. 32.-P. 84-91.

46. Kwong K. Y. and Hung M. C. A novel splice variant of HER2 with increased transformation activity//Mol. Carcinog.-1998.-V. 23.-P. 62-68.

47. Liu N., Furukawa T., Kobari M., and Tsao M. S. Comparative phenotypic studies of duct epithelial cell lines derived from normal human pancreas and pancreatic carcinoma//Am. J. Pathol.-1998.-V. 153.-P. 263-269.

48. Loir B., Perez S. C., Ghanem G., Lozano J. A., Garcia-Borron J. C., and Jimenez-Cervantes C. Expression of the MC1 receptor gene in normal and malignant human melanocytes. A semiquantitative RT-PCR study//Cell Mol Biol. (Noisy.-le-grand)-1999.-V. 45.-P. 1083-1092.

49. Maggiora P., Marchio S., Stella M. C., Giai M., Belfiore A., De Bortoli M., Di Renzo M. F., Costantino A., Sismondi P., and Comoglio P. M. Overexpression of the RON gene in human breast carcinoma//Oncogene-1998.-V. 16.-P. 2927-2933.

50. Mantovani L. T., Miotti S., Menard S., Canevari S., Raspagliesi F., Bottini C., Bottero F., and Colnaghi M. I. Folate binding protein distribution in normal tissues and biological fluids from ovarian carcinoma patients as detected by the monoclonal antibodies MOv18 and MOv19//Eur J Cancer-1994.-V. 30A.-P. 363-369.

51. McLeskey S. W., Ding I. Y., Lippman M. E., and Kern F. G. MDA-MB-134 breast carcinoma cells overexpress fibroblast growth factor (FGF) receptors and are growth-inhibited by FGF ligands//Cancer Res.-1994.-V. 54.-P. 523-530.

52. Morrison R. S., Yamaguchi F., Bruner J. M., Tang M., McKeehan W., and Berger M. S. Fibroblast growth factor receptor gene expression and immunoreactivity are elevated in human glioblastoma multiforme//Cancer Res.-1994.-V. 54.-P. 2794-2799.

53. Mrhalova M., Plzak J., Betka J., and Kodet R. Epidermal growth factor receptor—its expression and copy numbers of EGFR gene in patients with head and neck squamous cell carcinomas//Neoplasma-2005.-V. 52.-P. 338-343.

54. Mueller R. E., Parkes R. K., Andrulis I., and O'Malley F. P. Amplification of the TOP2A gene does not predict high levels of topoisomerase II alpha protein in human breast tumor samples//Genes Chromosomes. Cancer-2004.-V. 39.-P. 288-297.

55. Nakamura H., Saji H., Ogata A., Hosaka M., Hagiwara M., Kawasaki N., and Kato H. Correlation between encoded protein overexpression and copy number of the HER2 gene with survival in non-small cell lung cancer//Int. J. Cancer-2003.-V. 103.-P. 61-66.

56. Nouri A. M., Thompson C., Cannell H., Symes M., Purkiss S., and Amirghofran Z. Profile of epidermal growth factor receptor (EGFr) expression in human malignancies: effects of exposure to EGF and its biological influence on established human tumour cell lines//Int. J Mol. Med.-2000.-V. 6.-P. 495-500.

57. Ono Y., Nakanishi Y., Gotoh M., Sakamoto M., and Hirohashi S. Epidermal growth factor receptor gene amplification is correlated with laminin-5 gamma2 chain expression in oral squamous cell carcinoma cell lines//Cancer Lett.-2002.-V. 175.-P. 197-204.

58. Ouban A., Muraca P., Yeatman T., and Coppola D. Expression and distribution of insulin-like growth factor-1 receptor in human carcinomas//Hum. Pathol.-2003.-V. 34.-P. 803-808.

59. Pandini G., Vigneri R., Costantino A., Frasca F., Ippolito A., Fujita-Yamaguchi Y., Siddle K., Goldfine I. D., and Belfiore A. Insulin and Insulin-like Growth Factor-I (IGF-I) Receptor Overexpression in Breast Cancers Leads to Insulin/IGF-I Hybrid Receptor Overexpression: Evidence for a Second Mechanism of IGF-I Signaling//Clin Cancer Res-1999.-V. 5.-P. 1935-1944.

60. Peace B. E., Hughes M. J., Degen S. J., and Waltz S. E. Point mutations and overexpression of Ron induce transformation, tumor formation, and metastasis//Oncogene-2001.-V. 20.-P. 6142-6151.

61. Perez E. A., Roche P. C., Jenkins R. B., Reynolds C. A., Halling K. C., Ingle J. N., and Wold L. E. HER2 testing in patients with breast cancer: poor correlation between weak positivity by immunohistochemistry and gene amplification by fluorescence in situ hybridization//Mayo Clin. Proc.-2002.-V. 77.-P. 148-154.

62. Pollett J. B., Trudel S., Stern D., Li Z. H., and Stewart A. K. Overexpression of the myeloma-associated oncogene fibroblast growth factor receptor 3 confers dexamethasone resistance//Blood-2002.-V. 100.-P. 3819-3821.

63. Porte H., Triboulet J. P., Kotelevets L., Carrat F., Prevot S., Nordlinger B., DiGioia Y., Wurtz A., Comoglio P., Gespach C., and Chastre E. Overexpression of stromelysin-3, BM-40/SPARC, and MET genes in human esophageal carcinoma: implications for prognosis//Clin. Cancer Res.-1998.-V. 4.-P. 1375-1382.

64. Rikimaru K., Tadokoro K., Yamamoto T., Enomoto S., and Tsuchida N. Gene amplification and overexpression of epidermal growth factor receptor in squamous cell carcinoma of the head and neck//Head Neck-1992.-V. 14.-P. 8-13.

65. Ritter C. A. and Arteaga C. L. The epidermal growth factor receptor-tyrosine kinase: a promising therapeutic target in solid tumors//Semin. Oncol.-2003.-V. 30.-P. 3-11.

66. Saxby A. J., Nielsen A., Scarlett C. J., Clarkson A., Morey A., Gill A., and Smith R. C. Assessment of HER-2 status in pancreatic adenocarcinoma: correlation of immunohistochemistry, quantitative real-time RT-PCR, and FISH with aneuploidy and survival//Am. J. Surg. Pathol.-2005.-V. 29.-P. 1125-1134.

67. Scharf J. G. and Braulke T. The role of the IGF axis in hepatocarcinogenesis//Horm Metab Res-2003.-V. 35.-P. 685-693.

68. Sekharam M., Zhao H., Sun M., Fang Q., Zhang Q., Yuan Z., Dan H. C., Boulware D., Cheng J. Q., and Coppola D. Insulin-like Growth Factor 1 Receptor Enhances Invasion and Induces Resistance to Apoptosis of Colon Cancer Cells through the Akt/Bcl-xL Pathway//Cancer Res-2003.-V. 63.-P. 7708-7716.

69. Tatidis L., Masquelier M., and Vitols S. Elevated uptake of low density lipoprotein by drug resistant human leukemic cell lines//Biochem. Pharmacol.-2002.-V. 63.-P. 2169-2180.

70. Udart M., Utikal J., Krahn G. M., and Peter R. U. Chromosome 7 aneusomy. A marker for metastatic melanoma? Expression of the epidermal growth factor receptor gene and chromosome 7 aneusomy in nevi, primary malignant melanomas and metastases//Neoplasia.-2001.-V. 3.-P. 245-254.

71. Untawale S., Zorbas M. A., Hodgson C. P., Coffey R. J., Gallick G. E., North S. M., Wildrick D. M., Olive M., Blick M., Yeoman L. C., and. Transforming growth factor-alpha production and autoinduction in a colorectal carcinoma cell line (DiFi) with an amplified epidermal growth factor receptor gene//Cancer Res.-1993.-V. 53.-P. 1630-1636.

72. Vella V., Sciacca L., Pandini G., Mineo R., Squatrito S., Vigneri R., and Belfiore A. The IGF system in thyroid cancer: new concepts//Mol Pathol-2001.-V. 54.-P. 121-124.

73. Vitols S., Gunven P., Gruber A., and Larsson O. Expression of the low-density lipoprotein receptor, HMG-CoA reductase, and multidrug resistance (Mdr1) genes in colorectal carcinomas//Biochem. Pharmacol.-1996.-V. 52.-P. 127-131.

74. Walch E. T., Albino A. P., and Marchetti D. Correlation of overexpression of the low-affinity p75 neurotrophin receptor with augmented invasion and heparanase production in human malignant melanoma cells//Int. J. Cancer-1999.-V. 82.-P. 112-120.

75. Wang S. C., Zhang L., Hortobagyi G. N., and Hung M. C. Targeting HER2: recent developments and future directions for breast cancer patients//Semin. Oncol.-2001.-V. 28.-P. 21-29.

76. Weiner H. L. The role of growth factor receptors in central nervous system development and neoplasia//Neurosurgery-1995.-V. 37.-P. 179-193.

77. Weitman S. D., Lark R. H., Coney L. R., Fort D. W., Frasca V., Zurawski V. R., Jr., and Kamen B. A. Distribution of the folate receptor GP38 in normal and malignant cell lines and tissues//Cancer Res-1992.-V. 52.-P. 3396-3401.

78. Wikberg J. E., Muceniece R., Mandrika I., Prusis P., Lindblom J., Post C., and Skottner A. New aspects on the melanocortins and their receptors//Pharmacol. Res.-2000.-V. 42.-P. 393-420.

79. Xie Y., Skytting B., Nilsson G., Brodin B., and Larsson O. Expression of Insulin-like Growth Factor-1 Receptor in Synovial Sarcoma: Association with an Aggressive Phenotype//Cancer Res-1999.-V. 59.-P. 3588-3591.

80. Xu F. J., Stack S., Boyer C., O'Briant K., Whitaker R., Mills G. B., Yu Y. H., and Bast R. C., Jr. Heregulin and agonistic anti-p185(c-erbB2) antibodies inhibit proliferation but increase invasiveness of breast cancer cells that overexpress p185(c-erbB2): increased invasiveness may contribute to poor prognosis//Clin. Cancer Res.-1997.-V. 3.-P. 1629-1634.

81. Yu H. and Rohan T. Role of the Insulin-Like Growth Factor Family in Cancer Development and Progression//J Natl Cancer Inst-2000.-V. 92.-P. 1472-1489.

Although the above listing is detailed for ligands that target tumors, similar listing are available or can be compiled from the literature for other therapeutic areas, such as cardiovascular, neuroscience, inflammation, respiratory condition, HIV, infections generally, etc.

3. Selection of a Ligand Module

With the overexpressing receptor/surface protein target selected, the ligand module can be chosen. The ligand module has two functions in the MTP: 1) specific recognition of a target cell and 2) penetration into the target call via a selective receptor-mediated endocytosis. The ligand module can be chosen from a spectrum of available ligands to the selected, over-expressing receptors. One of skill in the art can readily select a suitable ligand based on the receptor selected, for example, by a literature search of ligands known to have an affinity for the receptor. For example, one online database that provides a listing of ligands is found at the European Bioinformatics Institute (ebi.ac.uk) which provides a listing of 9436 ligands (as of Jun. 8, 2011). The contents of this listing of ligands is incorporated herein by reference for its use in providing suitable ligands. The listing is described as giving all the complete molecules bound to protein or DNA/RNA in the structures in the Protein Data Bank (PDB), Europe. With this listing, one of skill in the art can search for a receptor of interest and find a suitable ligand to bind with the receptor. The specific internet address for listing of ligand molecules is found at:

ebi.ac.uk/thornton-srv/databases/cgi-bin/vctr/ligands search.pl-?template=tmplt33

If the receptor is a newly discovered receptor for which a listing of suitable ligands is not readily available, the researcher can experimentally determine a suitable ligand with affinity to the receptor. In choosing the ligand module, a number of factors must be considered. First, the ligand should possess optimal affinity to the receptor. For example, the ligand should be selective for the particular receptor or for a very limited number of receptors. Because one objective of the MTP is to target the MTP to specific cells, ligand selectivity provides benefits to the efficacy and safety of the product. If the ligand can be chosen so that it is very selective to a particular receptor, this will reduce the risk of side effects caused by the ligand and MTP binding to receptors on non-target cells. As a more specific example of the need for selective ligands, consider the delivery of RNA or DNA in gene therapy. If the ligand is not sufficiently selective, the MTP will be delivered to a cell that should not be targeted. If the RNA or DNA is delivered to a cell type that would be damaged by the gene therapy, the patient could suffer catastrophic consequences.

Second, the ligand should be capable of permitting modification without significant changes of its affinity to the receptors. The ligand may be modified, for example, upon being incorporated in the MTP, thereby potentially affecting its affinity.

Also part of this step is the analysis of whether or not to include a spacer between the ligand module and the remaining portions of the MTP moiety. This analysis is based on knowing the properties of the selected over-expressed receptor, its ligand, and position of the ligand within the MTP moiety. For example, the active site of melanocortin receptors is deep within their structure [Prusis, P., Schioth H. B., Muceniece R., Herzyk P., Afshar M., Hubbard R. E., Wikberg J. E. S. Modeling of the three-dimensional structure of the human melanocortin 1 receptor, using an automated method and docking of a rigid cyclic melanocyte-stimulating hormone core peptide. J. Mol. Graphics. Modelling 15:307-317, 1997; Yang X., Wang Z., Dong W., Ling L., Yang H., Chen R. Modeling and Docking of the Three-Dimensional Structure of the Human Melanocortin 4 Receptor. J. Protein Chem., 2003, 22:335-344; Lapinsh M., Veiksina S., Uhlen S., Petrovska R., Mutule I., Mutulis F., Yahorava S., Prusis P., Wikberg J. E. Proteochemometric mapping of the interaction of organic compounds with melanocortin receptor subtypes. Mol. Pharmacol. 2005; 67(1):50-59], so one needs to provide more spatial freedom to α-melanocyte-stimulating hormone residue (the ligand module) within the MTP in order not to decrease its affinity to the receptor active site. By knowing the properties of the receptor, the decision is made as to whether or not a spacer should be used to increase the specificity of the MTP for the receptor.

4. Inclusion of One or More Specialized Modules for Multilevel Specificity

The next step is the analysis and design needed to provide specialized modules within the MTP moiety to target other stages of multilevel specificity for ensuring MTP penetration into the target cell. One such module is an endosomolytic module. An endosomolytic module is defined herein as a module which "disrupts" endocytotic vesicles within a proper amount of time before MTP degradation within the vesicles. The MTP is in the vesicle as a result of receptor-mediated endocytosis. In designing the endosomolytic module, a polypeptide or its fragment is chosen from a spectrum of known polypeptides/proteins that enables penetration of the polypeptide/protein or its part through cell membranes at endosomal pHs. The polypeptide or its fragment should have the property that it is inactive at a pH of 7-7.4 (usual extracellular pH) but is active at the lower, more acidic pH (typical for endocytotic vesicles). At the lower pH, the polypeptide has a change in conformation that results in the formation of openings into the vesicle. The formation of openings in the membrane causes instability of the vesicle and its ultimate breakdown, thereby releasing the MTP into the cell interior.

In general, therefore, the protein, polypeptide or fragment thereof should have the property of being capable of disintegrating of the membrane wall of the vesicle such that the MTP is released into the cell. Preferably, the protein, polypeptide or fragment will accomplish this function by a conformational change at a lower pH characteristic of the internal fluid of the endosome while being inactive at a higher pH characteristic of the bodily fluid through which the MTP is delivered. Such proteins are readily determined by those of skill in the art by conducting a search of the literature. Such proteins (or polypeptides or fragments) can be natural or artificial.

As an example, sequences of the following membrane-active peptides could also be used: GALA (WEAALAEALAEALAEHLAEALAEALEALAA) (SEQIDNO:1) [Li W, Nicol F, Szoka F C Jr. GALA: a designed synthetic pH-responsive amphipathic peptide with applications in drug and gene delivery. Adv Drug Deliv Rev. 2004; 56(7):967-985]; INF7 (GLFEAIEGFIENGWEGMIEGWYGCG) (SEQIDNO:2), H5WYG (GCGLFHAIAHFIHGGWHGLIHGWYG) (SEQIDNO:3) [Moore N M, Sheppard C L, Barbour T R, Sakiyama-Elbert S E. The effect of endosomal escape peptides on in vitro gene delivery of polyethylene glycol-based vehicles. J Gene Med. 2008; 10(10):1134-1149]; a fusogenic segment of glycoprotein H from herpes simplex virus (GLASTLTRWAHYNALIRAF) (SEOIDNO:4) [Tu Y, Kim J S. A fusogenic segment of glycoprotein H from herpes simplex virus enhances transfection efficiency of cationic liposomes. J Gene Med. 2008; 10(6):646-654].

As explained above, this module becomes membrane active only under special conditions, namely, in a slightly acidic milieau. For example, the activity of the module may have an activity maxima at pH 5.5. This action of this module has been shown to give a pore formation in lipid bilayers by the MTP under these conditions. Moreover, it should be understood that the pore formation as well as an endosomal/lysosomal activity at pH 3-pH 6 is a result of combined actions of two MTP modules, namely the endosomolytic module and the carrier module.

A second specialized module is selected for intracellular transportation to ensure delivery of the MTP to a specific subcellular compartment by the cellular transport machinery. Examples of such compartments include nucleus, nucleolus, endocytotic vesicles, endoplasmic reticulum, Golgi apparatus, hyaloplasm etc. In designing the module for intracellular transportation, an amino-acid sequence is chosen from a spectrum of known sequences of polypeptides/proteins that ensures intracellular transport of these polypeptides/proteins into a desired subcellular target compartment. The selected amino-acid sequence is determined based on the targeted subcellular compartment. As noted above, such amino acid sequences are known in the art and any sequence that targets the particular subcellular compartment is suitable. The sequence may be found by searching the literature for amino-acid sequences that target specific organelles.

For example, if the nucleus is selected as a specific compartment, the suitable sequences can be found in the database of nuclear localization signals (NLSdb, rostlab.org/services/nlsdb/). A moiety of interest for tumor cell-enhanced nuclear accumulation is the "T-NLS" from chicken anemia virus (CAV) viral protein 3 (VP3) or apoptin (residues 74-121) where tumor cell-specific phosphorylation at the T108 site inactivates nuclear export, leading to higher nuclear accumulation in tumor cells [Poon I K, Oro C, Dias M M, Zhang J, Jans D A. Apoptin nuclear accumulation is modulated by a CRM1-recognized nuclear export signal that is active in normal but not in tumor cells. Cancer Res. 2005; 65(16): 7059-7064; Kuusisto H V, Wagstaff K M, Alvisi G, Jans D A. The C-terminus of apoptin represents a unique tumor cell-enhanced nuclear targeting module. Int J Cancer. 2008; 123 (12): 2965-2969]. Alternatively, optimized or modified NLSs can be used such as the optimized NLS of Simian Virus SV40 large tumor antigen (opT-NLS): SSDDEATADSQHaaPP-KKKRKV [Akhlynina T V, Rosenkranz A A, Jans D A, Statsiuk N V, Balashova I Yu, Toth G, Pavo I, Rubin A B, Sobolev A S. Nuclear targeting of chlorin $e_6$ enhances its photosensitizing activity. J. Biol. Chem. 1997, 272: 20328-20331], where the sequence of T-antigen amino acids 111-132 has been substituted at positions 123 and 124 (ST substituted by AA) to inactivate the nuclear transport inhibitory cyclin dependent kinase phosphorylation site at T124 [Fulcher A J, Roth D M, Fatima S, Alvisi G, Jans D A. The BRCA-1 binding protein BRAP2 is a novel, negative regulator of nuclear import of viral proteins, dependent on phosphorylation flanking the nuclear localization signal. FASEB J. 2010; 24(5):1454-1466].

A third specialized module may be selected for specific recognition of specific intracellular macromolecules by the MTP. Examples of intracellular macromolecules that can be targeted include DNA, RNA, proteins, carbohydrates etc. In designing the module for subcellular recognition, a polypeptide or its fragment is chosen from a spectrum of known polypeptides/proteins that enables optimal specific binding to a specified type of molecule within a given compartment of the target cell. In effect, the second specialized module causes the MTP to be transported to a specific organelle and the third specialized module causes the MTP to bind to the organelle.

For example, the online database, FootprintDB, provides a listing of DNA-binding polypeptide motifs is found at the Estación Experimental de Aula Dei (EEAD) (floresta.eead.csic.es/footprintdb/? documentation), offering 4760 amino-acid motifs (as of Jun. 17, 2011). Proteins, not antibodies, which interact with another proteins can be found in the web-based Protein Interaction Network Analysis platform (PINA), which integrates protein-protein interaction data from six databases and provides network construction, filtering, analysis and visualization tools. Its Internet address is csbi.ltdk.helsinki.fi/pina/home.do. Proteins specifically interacting with carbohydrate moieties can be found at the Bioinformatics Centre of the Indian Institute of Science, in the Lectin Database, LectinDB (proline.physics.iisc.ernet.in/home/Software_and_Databases#Lectin_Database). Many intracellular molecules can be targeted with the use of antibodies which can be included into the MTP in different forms including nanobodies, mono- or bispecific diabodies etc.

A fourth specialized module is selected for retention, i.e. prolonged localization, of the MTP in the desired compartments of the target but not of the non-target cells. For example, longer retention of the MTP within the most vulnerable compartment of cancer cells (it is usually the cell nucleus), if compared with non-cancer ones, can enhance both selectivity and efficiency of anti-cancer drugs carried by the MTP. Specific phosphorylation of the aforementioned CAV VP3 (apoptin) in many cancer cells results in loss of its ability to leave the cell nuclei; this leads to its retention within the cancer-cell nuclei in contrast to the normal cells (Alvisi G., Poon I. K. H., Jans D. A. Tumor-specific nuclear targeting: Promises for anti-cancer therapy? Drug Resistance Updates, 2006, 9: 40-50).

Another suitable example is an amino acid sequence providing proteasome inhibition. Two examples of such amino acid sequences are PI31 and PR39, as provided below:

PI31 protein sequence: $V^{192}$ VGEDLDPFGPRRG-GMIVDPLRSGFPRALIDPSSGLP NRLPPGAVPP-GARFDPFGPIGTSPPGPNPDHLPPPGYDDMYL$^{271}$ (SEOIDNO. 6) [McCutchen-Maloney S L, Matsuda K, Shimbara N, Binns D D, Tanaka K, Slaughter C A, DeMartino G N. cDNA cloning, expression, and functional characterization of P131, a proline-rich inhibitor of the proteasome. J Biol Chem. 2000; 275(24):18557-18565, the contents of which are incorporated herein by reference in their entirety for the disclosure of the PI31 protein sequence, its preparation and use].

PR39 derivative: RRRPRPPYLPRW (SEQIDNO. 7) [Anbanandam A, Albarado D C, Tirziu D C, Simons M, Veeraraghavan S. Molecular basis for proline- and arginine-rich peptide inhibition of proteasome. J Mol Biol. 2008; 384(1): 219-227, the contents of which are incorporated herein by reference in their entirety for the disclosure of the PR39 derivative, its preparation and use]. This module can contribute to: (i) enhancement of efficiency of delivery by inhibition of proteasomal degradation of the MTP, and (ii) additional cancer-cell specificity [Eldridge AG, O'Brien T. Therapeutic strategies within the ubiquitin proteasome system. Cell Death Differ. 2010, 17:4-13; McConkey D J, Zhu K. Mechanisms of proteasome inhibitor action and resistance in cancer. Drug Resist Updat. 2008, 11:164-179, the contents of both of which are incorporated herein by reference in their entirety for the disclosure of use of the ubiquitin proteasome system and proteasome inhibitor action and resistance in cancer].

A fifth specialized module, a carrier module, is selected to bring the modules together and link them to the transported active substance(s). In designing the carrier module, a polypeptide or its fragment is chosen from a spectrum of known polypeptides/proteins. The polypeptides/proteins are selected to provide optimal spatial distribution of other MTP modules, a high yield of a soluble MTP during its biosynthesis, and/or a covalent or non-covalent attachment of the substance to be transported. The last function, non-covalent attachment, could be accomplished in the case of e.g. amino-acid "pockets" in the module moiety that have a high affinity to certain molecules, like bacterial hemoglobin-like proteins which have hydrophobic pockets for porphyrin-like molecules. These molecules can be used directly or after their chemical modifications as carriers/chelators etc. for substances to be transported after having been inserted into the pocket of the fifth module. Such polypeptides can be found in many protein databases including the RCSB PDB (www.pdb.org).

5. Determining Necessity of Specific Modules According to Specific Goals of the MTP A general scheme for determining the necessity of using specific modules according to specific goals of the MTP:

i. different special modules for intracellular transportation should be chosen depending on a targeted subcellular compartment (usually not endosomes, lysosomes and the hyaloplasm);

ii. the endosomolytic module should be included in the MTP moiety if endosomes/lysosomes are not targeted subcellular compartments;

iii. the module for subcellular recognition should be included in the MTP moiety if MTP binding to specific (macro)molecules within target subcellular compartment is necessary;

iv. the ligand module is defined by a target cell type and is obligatory if cell specificity is required; if such specificity is not required or a wide range of cell types is the target, one should select a ligand to overexpressed internalizable receptors that are maximally represented on the desired cell types;

v. the carrier module is desirable for most MTP applications.

6. Process for Assembling the Various Modules into the MTP

The process of assembling the modules into the MTP involves a step of using plasmids to encode each module that is to be produced. The various plasmids are assembled into a final plasmid encoding the entire MTP by consecutive cloning, as is known in the art. The sequence of the assembling should take into account the features or function of each module (e.g., ligand module, described above). For example, substitutions/modifications of the C-terminus of α-melanocyte-stimulating hormone significantly decreases its binding affinity to its receptor, whereas modifications of its N-terminus do influence its activity [Sahm, U. G., Olivier, G. W., Branch, S. K., Moss, S. H., and Pouton, C. W. Influence of alpha-MSH terminal amino acids on binding affinity and biological activity in melanoma cells. Peptides, 1994, 15: 441-446]. So, if one needs to use α-melanocyte-stimulating hormone as a ligand module, this oligopeptide should be put at the C-terminus of the MTP. The number of modules and their function varies depending on the final goal of delivery, described generally above. The full-sized or complete MTP can be produced biosynthetically either as a single molecule or in its part (e.g., without the ligand module) to which missing module(s) (e.g., the missing ligand module) may be attached covalently or non-covalently.

7. Process for Attaching the MTP and Substances to be Delivered by the MTP

The process of attaching the MTP and substances to be delivered by the MTP may be by covalent or non-covalent attachment with a number of variations. For example, the substances to be transported can be attached to the MTP directly either covalently (e.g., with bifunctional cross-linking reagents) directly or with a spacer. The substances to be transported may be non-covalently attached to the MTP (e.g., by insertion into a "pocket" of the carrier module as a part of a cyclic tetrapyrrol molecule or via attachment of the substance to the cyclic tetrapyrrol molecule). The substances to be transported may be attached covalently to a non-covalently attached spacer (e.g., to a spacer inserted into a "pocket" in the carrier module). The substances to be transported may be attached non-covalently to a covalently attached spacer (e.g., to a spacer attached with bifunctional cross-linking reagents).

Therapeutic, Diagnostic, and Research Applications of the MTP

There are numerous therapeutic, diagnostic and research applications of the MTP. For example, the MTP can be applied in medicine, experimental biology, and veterinary use, to name but a few. For example, in medicine, the MTP can be used in oncology applications, such as head-and-neck cancer, esophageal cancer, glioblastoma, bladder cancer, etc. The MTP also can be applied in cardiology, e.g., ablation of atherosclerotic plaques; viral diseases (e.g., elimination of host cells, inhibition of virion synthesis, e.g., for HIV treatment); gynecology (e.g., endometriosis), to name but a few potential medicinal applications. In medicinal diagnostics, the MTP can be used for the same diseases where a therapeutic usage of the MTP is possible. The MTP may, therefore, be used as a tool in theranostics, where diagnostic and therapeutic means are combined in one platform. The MTP also can be used in gene therapy procedures to deliver RNA or DNA with specificity to a particular type of cell. As explained above, the MTP concept described herein provides a means to more specifically target a therapeutic agent to particular cells based on affinity of a ligand for a particular receptor. The MTP also can be used in research applications, such as when it is desired to place an active substance within a specific cell type and/or within a specific cell compartment.

In experimental biology applications, the application is possible as a vehicle for delivery of different biologically active substances into specific subcellular compartments with research purposes. In veterinary applications, the MTP concept may be applied in therapeutic and diagnostic applications, e.g., oncological conditions and others.

Table 1 compares the main characteristics of the MTP to other drug delivery vehicles, namely, antibodies, liposomes, and nanoparticles.

TABLE 1

A comparison of main characteristics of the MTP and other drug delivery vehicles

| Property | MTP | Antibodies | Liposomes | Nanoparticles |
|---|---|---|---|---|
| High yield | ++ | ± | ++ | ++ |
| Simplicity of purification | ++ | ± | ± | |
| Biodegradability | ++ | ++ | + | ± |
| Production cost | ++ | ± | + | + |
| Possibility to be freeze-dried and reconstituted without loss of activity | ++ | ± | — | not applicable |
| Long shelf-life | ++ | ± | — | ++ |
| Possibility to quickly replace target cells | ++ | — | ± | ± |
| Possibility to deliver different types of substances | ++ | + | ++ | ± |

++, the property is present;
+, the property is present under certain conditions/composition of a vehicle and a substance;
±, realization is difficult;
—, the property cannot be realized.

Example 1

Use of a MTP to Treat Tumors with Overexpression of EGFR

The following example provides one implementation of the above process of designing a MTP. The example is specific to a head or neck cancer, glioblastoma multiforme tumors, etc., which have an overexpression of epidermal growth factor receptors (EGFR) on the tumor cells. Therefore, this pathology is suitable for treatment using the MTP concept. The general principles described below can be applied to other pathologies that are suitable to treatment using the MTP concept described herein.

1. Selection of Pathologies to be Targeted

The first step involves determining a treatment benefiting from a targeted delivery of therapeutic substances to defined subcellular compartments of target cells. Pathologies that will benefit from a targeted delivery include a glioblastoma multiforme, a head or neck cancer, or a severe brain tumor. In this example, the glioblastoma multiforme tumor is selected for treatment by preparing a MTP to deliver a ligand suitable for treating the tumor.

2. Identification of Internalizable Receptors

The second step of the process involves identifying internalizable receptors based on finding internalizable receptors that are overexpressed on target cells at the given pathology. The literature (e.g., more than several hundred publications) includes lists of receptors over-expressed in tumor cells. For example, a receptor to Epidermal Growth Factor (EGF), or EGF receptor (EGFR), and its variant EGFRvIII is disclosed in the literature [see, e.g., Loew S. et al. The epidermal growth factor receptor as a therapeutic target in glioblastoma multiforme and other malignant neoplasms. Anticancer Agents Med. Chem. 2009, 9(6):703-715].

In another embodiment, the MTP can include a ligand module for the following receptors: melanocortin receptor-1 (e.g. melanoma), somatostatin receptor (e.g. medulloblastoma), IL3 receptor (e.g. acute myeloid leukemia); MTP carrying internalizable antibodies against Her2/neu and Her3 (e.g. breast cancer). Therefore, because these pathologies have internalizable receptors that can be targeted, these pathologies can be treated using the MTP system described herein. It should be understood that the above listing of receptors is not exhaustive and internalizable receptors, in general, are suitable for targeting by the MTP.

3. Design of a Ligand Module

The third step involves the design of a ligand module of the MTP. As explained above, the ligand must be selected to provide optimal affinity to the over-expressing receptor and be modifiable without significant changes to its affinity for the receptor. Then, with knowledge of the receptor, there must be an analysis of whether or not to insert a spacer between the ligand module and the remaining part of the MTP moiety. Importantly, in the process one must decide whether it is necessary to make the MTP non-specifically penetrating into the cells, e.g. to place a cell-penetrating peptide instead of ligand module. Such a peptide may be included when one needs to process all the cells accessible for the MTP, e.g., for gene therapy ex vivo or for research purposes (e.g., MTP as a tool for an investigator etc.). Similarly, one must decide whether it is necessary to provide a post-translational treatment or modification of the selected ligand module. In some cases, post-translational treatment can enhance efficiency/functionality of some MTP modules, e.g., refolding can enhance binding affinity of several ligand modules (such as EGF). Another example is a post-translational addition of a ligand module to a "blank" MTP (see below).

In the example of the EGFR, the overexpression of EGFR in multiple types of cancer cells needs to be taken into account. Specifically, because EGFR is overexpressed not only on glioblastoma cells but also on some other types of cancer cells, it is reasonable to choose a ligand to EGFR but not to its variant EGFRIII. EGF can be easily modified at its N-terminus, so it can be put on the C-terminus of the future MTP. The gene encoding EGF can be taken from a cDNA library, or purchased. For example, it may be possible to use a previously produced genetic construct to obtain this gene. For EGF, the disclosure of Russian Patent No. 93031156 was used to produce this genetic construct. In this example, a spacer, $(Gly\text{-}Ser)_5$, was included between EGF and the rest of the MTP. The spacer is used to provide more spatial freedom for MTP modules which provides e.g. either higher binding affinity to the MTP or better accessibility to the MTP for intracellular macromolecules that should interact with the MTP.

4. Inclusion of One or More Specialized Modules for Multilevel Specificity

The next step is the analysis and design needed to provide specialized modules within the MTP moiety to target other stages of multilevel specificity for ensuring MTP penetration into the target cell. As explained above, one such module is an endosomolytic module and can be a repeated amphiphilic sequence such as GALA or diphtheria toxin translocation domain.

A second module selected is for intracellular transportation to ensure delivery of the MTP to a specific subcellular compartment by cellular transport machinery. Examples of such modules include nuclear targeting moieties; the opT-NLS from SV40 large T-antigen, or the CAV VP3 (apoptin) T-NLS residues 74-121, where an additional specificity level that can be achieved with preferential accumulation within cancer cells.

A fourth specialized module, a carrier module, is selected for linking/bringing together the modules with the transported substance(s). One such carrier module is *E. coli* hemoglobin-like protein HMP. A valuable property of an MTP containing the *E. coli* hemoglobin-like protein HMP as a carrier module is demonstrated when the MTP also contains a fragment of diphtheria toxin translocation domain as an endosomolytic module. This combination provides the ability to obtain the MTP in high concentrations at pH 7.5 and at more alkaline condition (as well as at pH 3.5 and lower). High concentrations of MTP in water solutions are important in order to provide high yield of conjugation of acting principles with the MTP. On the other hand the integration of HMP and a fragment of diphtheria toxin translocation domain provides MTP better endosomolytic ability. Furthermore the integration of HMP and a fragment of diphtheria toxin translocation domain broadens the range of membranolytic action. As illustrated in FIG. 5, this combination provides two ranges of high solubility of MTP—at a pH more than 7.5 as well as at a pH lower than 3.5. Between these pH values, the MTP demonstrate their endosomolytic activity, i.e., the MTP will be taken from the endosome through its membrane outside, into the hyaloplasm, at endosomal/lysosomal pHs.

Another valuable property of HMP is the presence of a hydrophobic pocket that can bind porphyrins, such as protoporphyrin IX, with high affinity. This property permits attachment of substances to be transported to the MTP non-covalently, using 'a mix-and-apply' approach. For example, protoporphyrin IX or its analogue/derivative can be used directly e.g. as a chelator of a radionuclide or indirectly, after derivatization which permits to obtain e.g. a derivative that is able either to chelate a radionuclide or to react with a substance to be transported. Thereafter the derivatized porphyrin molecule (with either radionuclide or the pharmaceutical) can be added to the MTP in stoichiometric amounts in order to obtain a final MTP carrying the pharmaceutical/radionuclide.

The module for intracellular transportation (in this case for transportation into the cell nucleus) is generated by PCR. The ligand module (EGF) is generated by PCR using the plasmid DNA containing the cloned EGF. The $(Gly\text{-}Ser)_5$ spacer is generated synthetically from oligonucleotides. The carrier module (HMP, hemoglobin-like protein from *E. coli*) is generated by PCR using *E. coli* chromosomal DNA as the template. The translocation domain of diphtheria toxin together with the natural spacer between the toxin domains (the endosomolytic module) is similarly generated by PCR using plasmid DNA containing the cloned diphtheria toxin gene as a template.

5. Determining Necessity of Specific Modules According to Specific Goals of the MTP Next, the MTP must be designed to deliver the therapeutic agent to the specific site through the use of specific modules. In this example of providing a cancer treatment to gliablastoma multiforme tumors and other EGFR overexpressing tumors, the final subcellular goal is the cell nucleus, which is one of the most sensitive subcellular compartments to many anticancer pharmaceutical agents. The cell nucleus contains most of a cell's genetic material, organized as multiple long linear DNA molecules in complex with a large variety of proteins. Therefore the endosomolytic module is obligatory for effect of acting principles, such as alpha-emitters, but a module for subcellular recognition is not necessary because one has no need to define a special intranuclear macromolecule since alpha-particles move randomly and possess sufficient range in order to achieve any intranuclear macromolecule. An opposite situation occurs in the event of, e.g., Auger electron-emitters because Auger electrons have a short range, their main target is nuclear DNA, so the MTP should also possess a module for subcellular DNA recognition.

6. Process for Assembling the Various Modules into the MTP

The process of assembling the various modules into the MTP involves a step of using plasmids to encode each module that is to be produced. As explained above, the various plasmids are assembled into a final plasmid encoding the entire MTP by consecutive cloning, as is known in the art. In this specific example, the gene modules encoding the corresponding peptide modules were designed according to the scheme:

BamHI site-module sequence-BgIII site-stop codon-HindIII site in order to maximize the flexibility of MTP for drug development. This structure is selected because it allows every gene module to be placed at any position along the hybrid gene due to the fact that it is flanked with BamHI and Bg111 restriction sites with identical sticky ends. All of the constructs are assembled through consecutive cloning and the strong T5 bacteriophage promoter was used for protein expression in bacteria. The plasmid construction for DTox-HMP-NLS-EGF, an EGFR-targeted MTP, is detailed in FIG. 6 and summarized here: The NLS module is generated by PCR using Deep Vent polymerase (Promega), the primers 5'-GTGAGATCTGGGTTCTTCTACCTTTCTCTTC-3' (SEQIDNO. 8) (forward) and 5'-GTG AGATCTGCGCGTAATGAGCTCCTTGCAAAC-3' (SEQIDNO. 9) (reverse; restriction site underlined, here and below), and plasmid pPR28 as a template. The EGF module is generated by PCR using the primers 5'-GGGGGCCCGGGATCCAATTCCGATAGCGAGTGTCCTC-3' (SEQIDNO. 10) (forward) and 5'-CAAGGAGATGGATCCCAACAGTCCTCCGGACACGGGGCC-3' (SEQIDNO. 11) (reverse) and plasmid DNA containing the cloned EGF [Lunin, V. G., Sergienko, O. V., Khodun, M. -V. L., Bader, L. B., Karpov, V. A., and Tikhonenko, T. I. Method of preparing recombinant plasmids pC(Sp)nS encoding chimeric protein with somatostatin sequence. 1995, Russian Patent Number 2,031,121]. The $(Gly\text{-}Ser)_5$ spacer (sp) is generated synthetically from oligonucleotides. The oligonucleotide chains (forward, 5'-GATCCCCGGGTTCTGGCTCCGGCTCTGGTTCCGGTTCTGGCGCCAGATCTA-3'; (SEQIDNO. 12) reverse, 5'-AGCTTAGATCTGGCGCCAGAACCGGAACCAGAGCCGGAGCCAGAACCCGGG-3') (SEQIDNO. 13) were phosphorylated separately. The HMP module is generated by PCR using Taq polymerase (SibEnzyme), the PCR primers 5'-GCAAAAAAAGGGATCCCATATGCTTGACGCTC-3' (SEQIDNO. 14) (forward) and 5'-CCGGCAACTCTAGATCTCAGCACCTTATGCG-3' (SEOIDNO. 15) (reverse), and with *E. coli* chromosomal DNA as the template. The translocation domain of diphtheria toxin together with the natural spacer between the toxin domains (DTox module), residues 198-384 of the whole toxin, is similarly generated by Taq PCR using the primers 5'-GTAGGTGGATCCGGGTCATCCATAAATCTTGATTGG-3' (SEQIDNO. 16) (forward) and 5'-CCCGTCATCCGGAAATGGTTAAGATCTATGCCCCGG-3' (SEQIDNO. 17) (reverse) and plasmid DNA containing the cloned diphtheria toxin gene as a template.

Expression of the MTP from the encoding plasmid DNA is carried out in *E. coli* strain M15 (carrying plasmid pREP4) according to the QIAGEN (Hilden, Germany) protocol. The cells are lysed in 10 mM HEPES-NaOH (pH 7.5), 0.5% Triton X-100, 1 mM phenylmethanesulfonyl fluoride, 1.5 μg/ml aprotinin, 1 mg/ml lysozyme; sonicated at 40 kHz; and centrifuged at 17,000 rpm for 25 min. The MTPs are purified on Ni-NTA-agarose (QIAGEN) according to the standard procedure. Finally, the MTPs are dialyzed against 10 mM Na-phosphate buffer (pH 8) with 150 mM NaCl.

The MTPs HMP-NLS-DTox-EGF, HMP-NLS-DTox-EGF (spacer deleted), DTox-HMP-apo-EGF for nuclear localization in nuclei of tumor cells with EGFR overexpressing are produced in the same way. The DTox-HMP-EGF MTP for hyaloplasm localization as well as the HMP-EGF MTP for endolysosome localization of the same type tumor cells were also produced.

Likewise the MTPs DTox-HMP-NLS-αMSH for melanoma treatment, DTox-HMP-NLS-somatostatin for treatment of neuroendocrine tumors, DTox-HMP-NLS (the non-specific "blank MTP"), and other MTPs were created.

7. Process for Attaching the MTP and Substances to be Delivered by the MTP

The process of attaching the MTP and substances to be delivered by the MTP may be through covalent or non-covalent bonding with a number of variations, e.g., directly or with a spacer. Attachment depends on the pharmaceutical or therapeutic agent that is planned to be used. For example, a photosensitizer can be attached with the use of water-soluble carbodiimides. Then, the MTP with the attached pharmaceutical agent should be separated from any unreacted pharmaceutical agent and MTP.

Alternatively, a substance to be transported can be attached to the MTP with the use of the hydrophobic pocket in the carrier module, HMP (FIG. 7). FIG. 7A demonstrates one of such substances, azido-PEG-derivative of cobalt-chlorin. Insertion of this substance into the hydrophobic pocket can be registered by changes in its absorption spectrum (FIG. 7B). Analysis of its Soret band at different MTP concentrations with the use of non-linear regression (Origin 6 software) demonstrates dose-dependent changes in the share of the derivative inserted into the pocket (FIG. 7C). The obtained derivative-MTP complexes can be used for attachment of substances to be transported via "click-reactions" [see e.g., Jewett J C, Bertozzi C R. Cu-free click cycloaddition reactions in chemical biology. Chem Soc Rev. 2010, 39(4): 1272-1279]. The complexes are stable in biological fluids like blood plasma as demonstrated in FIG. 8.

Example 2

Use of a Posttranslational Modification for Enhancement of Affinity to Specific Cell Receptors In the example of EGFR, a posttranslational modification of MTP was made by refolding the human EGF-containing ligand module. It was found that by refolding the human EGF-containing ligand module there was an increase of affinity of the MTP to EGFR. The procedure followed in refolding the protein is as follows:

MTP (10 μM) was incubated on ice for 20 h in 10 mM sodium phosphate buffer, pH 8.0 with 150 mM NaCl, 1 mM EDTA, 0.5 mM phenylmethylsulfonyl fluoride, 2 mM oxidized glutathione, 0.67 mM reduced glutathione. After refolding, the MTP was extensively dialyzed against 10 mM sodium phosphate buffer with 150 mM NaCl. This treatment resulted in more than a two-fold increase of MTP affinity to EGFR. This result is illustrated in FIG. 1. FIG. 1 shows the effect of MTP posttranslational treatment on the affinity of its ligand module to the cell receptor by measuring displacement of [$^{125}$I]iodo-EGF (2 nM) by DTox-HMP-NLS-EGF before (♦) and after (▲) refolding from EGFR receptors of A431 human epidermoid carcinoma cells. The results show that [$^{125}$I]iodo-EGF is bound to A431 cell surface receptors with an affinity constant of 0.15±0.02 $nM^{-1}$. The affinity constants for MTP binding with receptor were 19±3 $pM^{-1}$ before refolding and 54±5 $pM^{-1}$ after refolding, i.e. affinity of MTP for EGFR increases more than 2.8 fold.

Example 3

The Module for Subcellular Recognition

A third module selected is for subcellular recognition. For example, the target of subcellular recognition may be cellular DNA. One suitable example of the third module to target cellular DNA is CAV VP3/apoptin (74-121), which can bind DNA. Results for the use of VP3 (74-121) are illustrated in FIGS. 3 and 4. FIG. 3 shows the results of a gel-shift assay for a MTP containing VP3 74-121, DTox-HMP-apo-EGF, and a MTP lacking such a fragment, DTox-HMP-NLS-EGF. FIG. 4 graphically represents the interaction of DTox-HMP-apo-EGF (left graph) and DTox-HMP-NLS-EGF (right graph) with plasmid DNA assayed using surface plasmon resonance method on an SA chip (BiaCore X). apo is apoptin 74-121.

Experiments were carried out using BiaCore-X device (SA-chip). Plasmid DNA (4.7 kb) was biotinylated with the use of biotine-11-dUTP and nonradioactive DNA labeling kit, Biotin-Randomprime. DNA was immobilized onto the sensor chip by injection of 60 μl of 5.5 pM plasmid solution for 30 min. Binding was measured by injecting a defined concentration of the MTP to SA chip with immobilized DNA at a flow rate of 10 μl/min in 10 mM HEPES/MES buffer pH 8 with 150 mM NaCl and 1 mM EDTA. The chip was regenerated by injection of 8 M urea for 1 min. The binding variables were computed by using the kinetic data analysis of the software (BIAevaluation 4.1) in the BIACORE system. The MTP had strong interaction with SA chip without DNA therefore the "Heterogeneous ligand—Parallel reactions" model was used. Values of association constants with non-modified chip ($K_a$=2.66·$10^5$ $M^{-1}$ for DTox-HMP-apo-EGF and 1.16·$10^4$ $M^{-1}$ for DTox-HMP-NLS-EGF, Langmiur binding) were measured in separate experiments and used as constants for the model. These results show that the MTP with the new module DTox-HMP-apo-EGF provides 23 folds higher affinity for DNA than the MTP DTox-HMP-NLS-EGF.

Example 4

An Application of Protein Splicing for MTP Generation

Next, it must be decided what type of ligand module joining should be chosen. There is a wide pool of ligands apart from MTP mentioned in example 1. For example, the joining may be via a genetic construct or a protein splicing to the C-terminus of a blank MTP (non-liganded MTP). As illustrated in FIGS. 2A-B, the ligand module can be attached to the MTP with the use of a blank MTP carrying the C-terminal intein-CBD (chitin-binding domain) module. [see e.g., Elleuche S, Pöggeler S. Inteins, Valuable Genetic Elements in Molecular Biology and Biotechnology. Appl Microbiol Biotechnol. 2010; 87(2):479-489]. This can be used both for MTP purification and module joining without addition of any additional or extra amino acid to the MTP. The process illustrated in FIGS. 2A-B shows the assembling of an MPT encoding plasmid possessing intein and CBD (chitin-binding domain)-encoding regions. The source of the intein sequence is the pTXB1 plasmid. The source of the non-ligand MTP sequence is the pR820 plasmid coding DTox-HMP-NLS (the "blank" MTP). The Intein-CBD was produced by PCR reaction from the pTXB 1 plasmid with subsequent addition of Bgl II and Hind III sites: Bgl II-Intein-CBP-Hind III. The product was then inserted into pR820 plasmid.

The final plasmid produced in this manner then is purified, for example, on chitin beads and then split with 2-mercaptoethanesulfonic acid to give a product that easily reacts with SH— groups. FIG. 2B illustrates these purification process steps. Referring to FIG. 2B, this purified non-liganded MTP can be liganded by any polypeptide ligand possessing N-terminal Cys, including e.g. diabodies or nanobodies (a whole MTP carrying this type of ligands cannot be produced directly in the cytoplasm of *E. coli*), cell-penetrating peptides for non-specific penetration, or peptide ligands with synthetic amino acid derivatives. It should be noted that production of a whole MTP with such peptides is complicated by a high toxicity of the products for *E. coli.*

Example 5

Properties and Applications In Vivo

The MTP produced according to the steps above was subjected to in vivo testing.

MTP Toxicity and Immunogenicity.

C57Black/6J mice (n=3,4-week observation) tolerated the highest achievable i.v. dose of DTox-HMP-NLS-αMSH (7.5 mg) without any signs of toxicity; higher MTP doses could not be evaluated because of limitations in MTP solubility. C57Black/6J mice (n=5, 2-wk observation) and Balb/c ByJIco-nu/nu mice (n=8, 4-week observation) also tolerated multiple i.v. injections of 4×2 mg DTox-HMP-NLS-αMSH and 6×3 mg DTox-HMP-NLS-EGF, respectively, with time intervals of 2-3 days between doses. This data shows that MTP is not toxic to mice when administered as a single-injection at the maximum achievable dose or when administered in multiple dose regimens.

Delayed-type hypersensitivity (DTH) reactions are often used as a correlation of immune response to administered polypeptides [Kublin J G, Lowitt M H, Hamilton R G, Oliveira G A, Nardin E H, Nussenzweig R S, et al. Delayed-type hypersensitivity in volunteers immunized with a synthetic multi-antigen peptide vaccine (PfCS-MAP1NYU) against *Plasmodium falciparum* sporozoites. Vaccine. 2002; 20:1853-1861]. Female C57Black/6J mice (n=11, 20-25 g) were injected subcutaneously (s.c.) with DTox-HMP-NLS-αMSH (60 μA 2 mg/ml Dulbecco's Modified Eagle Medium (DMEM) mixed with Freund's complete adjuvant (1:1, v/v, Sigma). After 5 days, one hind foot pad of each mouse was injected with DTox-HMP-NLS-αMSH (40 μA 2 mg/ml); the collateral foot was injected with only DMEM (experimental group). A control group of mice (n=8) were not injected with MTP/Freund's adjuvant. Edema was measured [Biondo C, Beninati C, Delfino D, Oggioni M, Mancuso G, Midiri A, at al. Identification and cloning of a cryptococcal deacetylase that produces protective immune responses. Infection Immunity. 2002; 70:2383-2391] 24 h later in the foot pads of the experimental ($m_{MNT,exp}$, and collateral, $m_{DMEM,exp}$) and control ($m_{DMEM,contr}$) groups and expressed as:

$$\Delta DTH\ \% = \left( \frac{m_{MTP,exp} - m_{DMEM,exp}}{m_{DMEM,exp}} - \frac{m_{MTP,exp} - m_{DMEM,contr}}{m_{DMEM,contr}} \right) \times 100\%$$

MTP administration induced a slight DTH in C57Black/6J mice injected with DTox-HMP-NLS-αMSH, 5.4%, with the difference between experimental and control groups not statistically significant. Generally, an increase over control of about 20% or more is considered to indicate an immunogenic response [Omata Y, Kamiya H, Kano R, Kobayashi Y, Maeda R, Saito A. Footpad reaction induced by *Neospora caninum* tachyzoite extract in infected BALB/c mice. Veterinary Parasitol. 2006; 139:102-108]. The lack of a statistically significant difference between the experimental and control groups suggests a low degree of immunogenicity for this MTP.

In Vivo Targeting.

Next, in vivo targeting was evaluated with an $^{125}$I-Labeled MTP. DTox-HMP-NLS-αMSH was labeled with $^{125}$I using the N-succinimidyl 3-[$^{125}$I]iodobenzoate reagent, a method that has been shown to decrease in vivo deiodination by up to two orders of magnitude compared with conventional electrophilic methods [Vaidyanathan G, Zalutsky M R. Preparation of N-succinimidyl 3-[*I]iodobenzoate: an agent for the indirect radioiodination of proteins. Nat Protocols. 2006; 1:707-713]. The $^{125}$I-labeled DTox-HMP-NLS-αMSH was injected i.v. into C57Black/6J mice that had mouse melanoma tumors derived from B16-F1 which express at about 10,000 αMSH receptors per cell [Siegrist W, Solca F, Stutz S, Giuffre L, Carrel S, Girard J, at al. Characterization of receptors for α-melanocyte-stimulating hormone on human melanoma cells. Cancer Res. 1989; 49:6352-16358]. The ratio of $^{125}$I activity in tumor relative to that in skin and muscle was chosen as a metric for evaluating in vivo targeting because these tissues are in proximity to melanoma and their collateral damage from photodynamic therapy should be avoided.

As shown in FIG. 9, the selectivity of $^{125}$I-labeled DTox-HMP-NLS-αMSH retention generally increases with time and with doses of MTP≥200 μg. In FIG. 9, the graph labeled A shows the effect of time on the tumor to non-tumor ratio with a dosage of 11 μg MTP dose. The graph labeled B shows the effect of MTP dose on tumor to non-tumor ratio at three hours post injection. The optimal dose seen for targeting at 3 hours was 214 μg for tumor:skin (9.8±1.8) and 850 μg for tumor: muscle (13.4±1.7). It should be noted that the maximum tumor:skin ratio determined for MTP is 3-8 times higher than those reported for free photosensitizer in this murine melanoma model [Woodburn K W, Fan Q, Kessel D, Luo Y, Young S W. Photodynamic therapy of B16F10 murine melanoma with Lutetium Texaphyrin. J Invest Dermatol. 1998; 110:746-751; Fabris C, Vicente M G, Hao E, Friso E, Borsetto L, Joni G, at al. Tumour-localizing and photosensitising properties of mesotetra(4-nidocarboranylphenyl)porphyrin (H2TCP). J Photochem Photobiol B. 2007; 89:131-138; Joni G, Soncin M, Friso E, Vicente M G, Hao E, Miotto G, at al. A novel boronated-porphyrin as a radio-sensitizing agent for boron neutron capture therapy of tumours: In vitro and in vivo studies. Appl Radiat Isotopes. 2009; 67(7-8 Suppl):5321-5324].

In Vivo Targeting of the MTP Evaluated by Immunohistochemistry.

In this evaluation, immunofluorescence analysis was performed to determine the in vivo distribution in tumor and neighboring tissue, and subcelullar localization of MTP three hours after intravenous injection in mice. In this evaluation, DTox-HMP-NLS-αMSH was injected i.v. into DBA/2 mice bearing Cloudman S91, which express about 5,000 αMSH receptors per cell [Siegrist W, Solca F, Stutz S, Giuffre L, Carrel S, Girard J, et al. Characterization of receptors for α-melanocyte-stimulating hormone on human melanoma cells. Cancer Res. 1989; 49:6352-16358].

FIGS. 10A-F show results of 10 μm tissue sections from DBA/2 mice bearing murine Cloudman melanoma S91 transformed with GFP (green fluorescent protein) receiving DTox-HMP-NLS-αMSH. FIGS. 10A-D show results of tumor and surrounding tissue section at a magnification of 40×. FIG. 10A shows the tissue sections stained with Alexa Fluor 555 staining for MTP (red); FIG. 10B shows GFP fluorescence from tumor cells (green); FIG. 10C shows DAPI staining of cell nuclei (blue); FIG. 10D is an overlay of FIGS. 10A-C. FIG. 10E shows a tumor section at a magnification of 63× with an overlay of DAPI fluorescence (blue) and MTP (red). FIG. 10F shows the percentage of fields (±SEM) with specific MTP signal in nuclei and cytoplasm of tumor and neighboring skin cells. FIG. 10G shows the staining of a 2-3 μm tumor section (63×) from Balb/c ByJIco-nu/nu mouse bearing human A431 epidermoid carcinoma three hours after intravenous injection of chlorin $e_6$-DTox-HMP-NLS-EGF; overlay of DAPI fluorescence (blue) and MTP (red). The scale bars in FIGS. 10D and E are 20 μm and the scale bar in FIG. 10G is 5 μm. Preferential accumulation of MTP in the tumor was observed at three hours after injection, which was distinguished from surrounding non-tumor tissue by GFP fluorescence of transfected melanoma cells.

A comparison of MTP to DAPI staining suggested that a considerable fraction of MTP accumulation in melanoma cells occurred in cell nuclei (FIGS. 10C-D). The percentage of fields exhibiting MTP signal in nuclei and cytoplasm of tumor and proximal skin cells also was evaluated. As shown in FIGS. 10E-F, more than 80% and nearly 100% of fields in melanoma had MTP signal in nuclei and cytoplasm, respectively, compared with values of less than 40% in skin. Similar results were obtained after i.v. injection of DTox-HMP-NLS-EGF to Balb/c ByJIco-nu/nu mice bearing EGFR-expressing human epidermoid carcinoma A431 xenografts—accumulation of the MTP in tumor cells with evidence for localization within the cell nuclei (FIG. 10G). These experiments confirm that MTP can be designed to undergo transport from the blood pool to their intended subcellular target in receptor expressing tumor cells in vivo.

In Vivo MTP Anti-Tumor Efficacy Using Photodynamic Therapy.

In order to evaluate the potential utility of MTP for enhancing the therapeutic efficacy of a drug that requires localization within the cell nucleus to be effective, photodynamic therapy (PDT) studies were performed in three different murine subcutaneous tumor models, with PDT initiated three hours after photosensitizer (PS) injection. The comparative efficacy of photodynamic therapy with bacteriochlorin p conjugated with DTox-HMP-NLS-αMSH MTP and free bacteriochlorin p is reported in FIGS. 11A-D.

The first experiment was performed in C57Black/6J mice with B16-F1 melanoma. FIG. 11A reports tumor growth, mean±SEM, with injection and illumination cycles indicated with arrows. The average tumor volumes are shown up to the last day when all animals were alive in a group. FIG. 11B provides the Kaplan-Meier survival curve. An 89% inhibition in tumor growth was observed with the bacteriochlorin p-DTox-HMP-NLS-αMSH conjugate while no significant effect was seen with free bacteriochlorin p (FIG. 11A). The median survival for mice receiving PS-MTP conjugate was 32.0±1.3 days compared with 17.0±1.5 days for the control group and 20.0±5.5 days for the bacteriochlorin group (FIG.

11B). The difference in survival between PS-MTP and each of two control groups was significant (p<0.01).

The second experiment utilized DBA/2 mice with Cloudman S91 melanoma. FIG. 11C reports tumor growth, mean±SEM with the injection and illumination cycles being indicated with arrows. The average tumor volumes are shown up to the last day when all animals were alive in a group. FIG. 11D provides the Kaplan-Meier survival curve. A 98% inhibition in tumor growth was observed with the bacteriochlorin p-DTox-HMP-NLS-αMSH conjugate relative to controls (93% relative to free PS) (FIG. 11C). The median survival for mice receiving PS-MTP conjugate was 56.0±18.6 days compared with 21.0±0.7 days for the control group and 31.0±1.3 days for the bacteriochlorin group (FIG. 11D).

The third experiment was performed with chlorin $e_6$-DTox-HMP-NLS-EGF in Balb/c ByJIco-nu/nu mice with A431 human epidermoid carcinoma xenografts. The DTox-HMP-NLS-EGF MTP inhibits A431 human epidermoid carcinoma growth and enhances survival of tumor-bearing Balb/c ByJIco-nu/nu mice compared with free chlorin $e_6$. FIG. 12A reports A431 tumor growth, mean±SEM with the injection and illumination cycles being indicated with arrows. The average tumor volumes are shown up to the last day when all animals were alive in a group. FIG. 12B provides the Kaplan-Meier survival curve. A 98% inhibition in tumor growth was observed with the chlorin $e_6$-DTox-HMP-NLS-EGF conjugate relative to controls (94% relative to free PS) (FIG. 12A). Median survival for mice in the control group was 20.0±0.4 days with all animals succumbing by 22 days (FIG. 12B). In contrast, 75% of animals remained alive at the end of the 92-day observation period in the chlorin $e_6$-DTox-HMP-NLS-EGF group compared with 20% in the chlorin $e_6$ group.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

What is claimed is:

1. A modular transport platform (MTP) comprising several functional polypeptide modules within one molecule, specifically configured to penetrate a target cell, deliver the modular transporting platform into the target cells, provide pH-dependent membrane disruption activity, directed intracellular transport into a target subcellular compartment of the target cell, and an active agent coupled within the modular transport platform, the molecule comprising:

a first, heterologous module for a non-covalent coupling and having a hydrophobic pocket, the first, heterologous module being an *E. coli* hemoglobin-like protein, HMP, prepared from a first sequence, and comprising a non-covalently coupled cyclic tetrapyrrol chlorin or chlorin derivative, wherein the chlorin or chlorin derivative is covalently coupled to the active agent, and the chlorin or chlorin derivative is inserted into the hydrophobic pocket in vitro;

a second, heterologous module prepared from a second sequence and configured to cause delivery of the MTP to a particular subcellular compartment, wherein the intracellular transport module delivers the MTP to the subcellular compartment based on one or more cellular transport mechanisms;

a third, heterologous module prepared from a third sequence and configured to prolong the localization of the modular transport platform within the target subcellular compartment by binding to a component within the subcellular compartment to retain the MTP within the subcellular compartment or by undergoing a chemical modification within the subcellular compartment to impede the ability of the MTP to be exported from the targeted subcellular compartment.

2. The modular transport platform of claim 1, further comprising one or more of:

(1) a fourth, heterologous ligand module prepared from a fourth sequence and configured to target a specific receptor on the surface of the target cell by providing specific recognition of the target cell;

(2) a fifth, heterologous endosomolytic module prepared from a fifth sequence and configured to provide a pH-dependent membrane disruption activity within the target cell to disrupt an endocytotic vesicle to release the MTP within the target cell;

(3) a sixth, heterologous module prepared from a sixth sequence and configured to provide subcellular recognition of an intracellular macromolecule; and (4) a carrier module for unifying the modules and coupling the modules with the transported substance.

3. The modular transport platform according to claim 1 wherein said active agent is a radionuclide.

4. The modular transport platform according to claim 1, wherein the MTP is bacterially synthesized as several separated components and then these components are integrated to form the MTP.

5. The modular transport platform according to claim 4, wherein the separated components are combined via intein.

6. The modular transport platform according to claim 2, wherein the ligand module accomplishing penetration of said modular transport platform into a target cell is bacterially synthesized.

7. The modular transport platform according to claim 2, wherein the ligand module accomplishing penetration of said modular transport platform into a target cell is chemically synthesized.

8. The modular transport platform according to claim 1, wherein said module with the function of intracellular retention of the modular transport platform within the subcellular compartment of the target cell interacts with specific structures (molecules) within the subcellular compartment.

9. The modular transport platform according to claim 8, wherein said module with the function of intracellular retention of the modular transport platform within the subcellular compartment of the target cell interacts with specific structures (molecules) within the cell nucleus.

10. The modular transport platform according to claim 8, wherein said module with the function of intracellular retention of the modular transport platform within the subcellular compartment of the target cell interacts with DNA.

11. The modular transport platform according to claim 8, wherein said module with the function of intracellular retention of the modular transport platform within the subcellular compartment of the target cell interacts with specific structures (molecules) within the hyaloplasm.

12. The modular transport platform according to claim 8, wherein said module with the function of intracellular retention of the modular transport platform within the subcellular compartment of the target cell interacts with proteasomes.

13. A method of delivering a therapeutic, diagnostic or research agent as a substance to be transported with the modular transport platform of claim 1 comprising functional modules within one molecule which accomplishes penetration of said modular transport platform into target cells;

pH-dependent membrane disruption activity within the target cells to release the modular transport platform;

directed intracellular transport into a targeted intracellular compartment;

addition of the substance to be transported to a module for a non-covalent coupling of cyclic tetrapyrrol molecules; and a module with a function of retention of said modular transport platform within the intracellular compartment of the target cell, the method comprising of a systemic infusion of said modular transport platform with the substance to be transported attached to the modular transport platform.

14. A method of drying, storage and reconstitution of the modular transport platform of claim 1, the method comprising using a buffer to obtain a functional modular transport platform after freeze-drying.

15. The modular transport platform of claim 1, further comprising:

(1) a fourth, heterologous ligand module prepared from a fourth sequence and configured to target a specific receptor on the surface of the target cell by providing specific recognition of the target cell;

(2) a fifth, heterologous endosomolytic module prepared from a fifth sequence and configured to provide a pH-dependent membrane disruption activity within the target cell to disrupt an endocytotic vesicle to release the MTP within the target cell;

(3) a sixth, heterologous module prepared from a sixth sequence and configured to provide subcellular recognition of an intracellular macromolecule;

(4) the active agent being a therapeutic, diagnostic or research agent as a substance to be transported by the MTP; and (5) a carrier module for unifying the modules and coupling the modules with the transported substance.

* * * * *

SEQUENCE LISTING

```
<160> NUMBER OF SEQ ID NOS: 17

<210> SEQ ID NO 1
<211> LENGTH: 30
<212> TYPE: PRT
<213> ORGANISM: Unknown
<220> FEATURE:
<223> OTHER INFORMATION: Li W, Nicol F, Szoka FC Jr. GALA: a designed
      synthetic pH-responsive amphipathic peptide with applications in
      drug and gene delivery. Adv Drug Deliv Rev. 2004;56(7):967-985

<400> SEQUENCE: 1

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30


<210> SEQ ID NO 2
<211> LENGTH: 25
<212> TYPE: PRT
<213> ORGANISM: Unknown
<220> FEATURE:
<223> OTHER INFORMATION: Moore NM, Sheppard CL, Barbour TR,
      Sakiyama-Elbert SE. The effect of endosomal escape peptides on in
      vitro gene delivery of polyethylene glycol-based vehicles. J Gene
      Med. 2008;10(10):1134-1149

<400> SEQUENCE: 2

Gly Leu Phe Glu Ala Ile Glu Gly Phe Ile Glu Asn Gly Trp Glu Gly
1               5                   10                  15

Met Ile Glu Gly Trp Tyr Gly Cys Gly
            20                  25


<210> SEQ ID NO 3
<211> LENGTH: 25
<212> TYPE: PRT
<213> ORGANISM: Unknown
<220> FEATURE:
<223> OTHER INFORMATION: Moore NM, Sheppard CL, Barbour TR,
      Sakiyama-Elbert SE. The effect of endosomal escape peptides on in
      vitro gene delivery of polyethylene glycol-based vehicles. J Gene
      Med. 2008;10(10):1134-1149

<400> SEQUENCE: 3
```

-continued

Gly Cys Gly Leu Phe His Ala Ile Ala His Phe Ile His Gly Gly Trp
1 5 10 15

His Gly Leu Ile His Gly Trp Tyr Gly
20 25

<210> SEQ ID NO 4
<211> LENGTH: 19
<212> TYPE: PRT
<213> ORGANISM: Unknown
<220> FEATURE:
<223> OTHER INFORMATION: Tu Y, Kim JS. A fusogenic segment of glycoprotein H from herpes simplex virus enhances transfection efficiency of cationic liposomes. J Gene Med. 2008;10(6):646-654

<400> SEQUENCE: 4

Gly Leu Ala Ser Thr Leu Thr Arg Trp Ala His Tyr Asn Ala Leu Ile
1 5 10 15

Arg Ala Phe

<210> SEQ ID NO 5
<211> LENGTH: 22
<212> TYPE: PRT
<213> ORGANISM: Unknown
<220> FEATURE:
<223> OTHER INFORMATION: Akhlynina TV, Rosenkranz AA, Jans DA, Statsiuk NV, Balashova IYu, Toth G, Pavo I, Rubin AB, Sobolev AS. Nuclear targeting of chlorin e6 enhances its photosensitizing activity. J. Biol. Chem. 1997, 272: 20328-20331

<400> SEQUENCE: 5

Ser Ser Asp Asp Glu Ala Thr Ala Asp Ser Gln His Ala Ala Pro Pro
1 5 10 15

Lys Lys Lys Arg Lys Val
20

<210> SEQ ID NO 6
<211> LENGTH: 79
<212> TYPE: PRT
<213> ORGANISM: Unknown
<220> FEATURE:
<223> OTHER INFORMATION: McCutchen -Maloney SL, Matsuda K, Shimbara N, Binns DD, Tanaka K, Slaughter CA, DeMartino GN. cDNA cloning, expression, and functional characterization of PI31, a proline-rich inhibitor of the proteasome. J Biol Chem. 2000;275(24):18557-18565

<400> SEQUENCE: 6

Val Gly Gly Glu Asp Leu Asp Pro Phe Gly Pro Arg Arg Gly Gly Met
1 5 10 15

Ile Val Asp Pro Leu Arg Ser Gly Phe Pro Arg Ala Leu Ile Asp Pro
20 25 30

Ser Ser Gly Leu Pro Asn Arg Leu Pro Pro Gly Ala Val Pro Pro Gly
35 40 45

Ala Arg Phe Asp Pro Phe Gly Pro Ile Gly Thr Ser Pro Pro Gly Pro
50 55 60

Asn Pro Asp His Leu Pro Pro Pro Gly Tyr Asp Asp Met Tyr Leu
65 70 75

<210> SEQ ID NO 7
<211> LENGTH: 12
<212> TYPE: PRT
<213> ORGANISM: Unknown
<220> FEATURE:
<223> OTHER INFORMATION: Anbanandam A, Albarado DC, Tirziu DC, Simons M, Veeraraghavan S. Molecular basis for proline- and arginine-rich peptide inhibition of proteasome. J Mol Biol. 2008;384(1):219-227

<400> SEQUENCE: 7

```
Arg Arg Arg Pro Arg Pro Pro Tyr Leu Pro Arg Trp
1               5                   10
```

<210> SEQ ID NO 8
<211> LENGTH: 31
<212> TYPE: PRT
<213> ORGANISM: Unknown
<220> FEATURE:
<223> OTHER INFORMATION: the primers 5' GTGAGATCTGGGTTCTTCTACCTTTCTCTTC 3' (forward)

<400> SEQUENCE: 8

```
Gly Thr Gly Ala Gly Ala Thr Cys Thr Gly Gly Gly Thr Thr Cys Thr
1               5                   10                  15

Thr Cys Thr Ala Cys Cys Thr Thr Thr Cys Thr Cys Thr Thr Cys
            20                  25                  30
```

<210> SEQ ID NO 9
<211> LENGTH: 33
<212> TYPE: PRT
<213> ORGANISM: Unknown
<220> FEATURE:
<223> OTHER INFORMATION: Deep Vent polymerase (Promega), the primers 5' GTGAGATCTGCGCGTAATGAGCTCCTTGCAAAC 3' (reverse)

<400> SEQUENCE: 9

```
Gly Thr Gly Ala Gly Ala Thr Cys Thr Gly Cys Gly Cys Gly Thr Ala
1               5                   10                  15

Ala Thr Gly Ala Gly Cys Thr Cys Cys Thr Thr Gly Cys Ala Ala Ala
            20                  25                  30

Cys
```

<210> SEQ ID NO 10
<211> LENGTH: 37
<212> TYPE: PRT
<213> ORGANISM: Unknown
<220> FEATURE:
<223> OTHER INFORMATION: The primers 5'-GGGGGCCCGGGATCCAATTCCGATAGCGAGTGTCCTC 3' (forward)

<400> SEQUENCE: 10

```
Gly Gly Gly Gly Gly Cys Cys Cys Gly Gly Gly Ala Thr Cys Cys Ala
1               5                   10                  15

Ala Thr Thr Cys Cys Gly Ala Thr Ala Gly Cys Gly Ala Gly Thr Gly
            20                  25                  30

Thr Cys Cys Thr Cys
        35
```

<210> SEQ ID NO 11
<211> LENGTH: 39
<212> TYPE: PRT
<213> ORGANISM: Unknown
<220> FEATURE:
<223> OTHER INFORMATION: The primer 5' CAAGGAGATGGATCCCAACAGTCCTCCGGACACGGGGCC-3' (reverse)

<400> SEQUENCE: 11

```
Cys Ala Ala Gly Gly Ala Gly Ala Thr Gly Gly Ala Thr Cys Cys Cys
1               5                   10                  15

Ala Ala Cys Ala Gly Thr Cys Cys Thr Cys Cys Gly Gly Ala Cys Ala
```

-continued 20 25 30

Cys Gly Gly Gly Gly Cys Cys
35

<210> SEQ ID NO 12
<211> LENGTH: 51
<212> TYPE: PRT
<213> ORGANISM: Unknown
<220> FEATURE:
<223> OTHER INFORMATION: The oligonucleotide chains (forward, 5'
GATCCCCGGGTTCTGGCTCCGGCTCTGGTTCCGGTTCTGGCGCCAGATCTA-3'

<400> SEQUENCE: 12

Gly Ala Thr Cys Cys Cys Cys Gly Gly Gly Thr Thr Cys Thr Gly Gly
1 5 10 15

Cys Thr Cys Cys Gly Gly Cys Thr Cys Thr Gly Gly Thr Thr Cys Cys
20 25 30

Gly Gly Thr Thr Cys Thr Gly Gly Cys Gly Cys Cys Ala Gly Ala Thr
35 40 45

Cys Thr Ala
50

<210> SEQ ID NO 13
<211> LENGTH: 51
<212> TYPE: PRT
<213> ORGANISM: Unknown
<220> FEATURE:
<223> OTHER INFORMATION: The oligonucleotide chains reverse, 5'
AGCTTAGATCTGGCGCCAGAACCGGAACCAGAGCCGGAGCCAGAACCCGGG 3'

<400> SEQUENCE: 13

Ala Gly Cys Thr Thr Ala Gly Ala Thr Cys Thr Gly Gly Cys Gly Cys
1 5 10 15

Cys Ala Gly Ala Ala Cys Cys Gly Gly Ala Ala Cys Cys Ala Gly Ala
20 25 30

Gly Cys Cys Gly Gly Ala Gly Cys Cys Ala Gly Ala Ala Cys Cys Cys
35 40 45

Gly Gly Gly
50

<210> SEQ ID NO 14
<211> LENGTH: 32
<212> TYPE: PRT
<213> ORGANISM: Unknown
<220> FEATURE:
<223> OTHER INFORMATION: PCR primers 5' GCAAAAAAAGGGATCCCATATGCTTGACGCTC
3' (forward)

<400> SEQUENCE: 14

Gly Cys Ala Ala Ala Ala Ala Ala Ala Gly Gly Gly Ala Thr Cys Cys
1 5 10 15

Cys Ala Thr Ala Thr Gly Cys Thr Thr Gly Ala Cys Gly Cys Thr Cys
20 25 30

<210> SEQ ID NO 15
<211> LENGTH: 31
<212> TYPE: PRT
<213> ORGANISM: Unknown
<220> FEATURE:
<223> OTHER INFORMATION: PCR primers and 5'
CCGGCAACTCTAGATCTCAGCACCTTATGCG 3' (reverse)

<400> SEQUENCE: 15

-continued

```
Cys Cys Gly Gly Cys Ala Ala Cys Thr Cys Thr Ala Gly Ala Thr Cys
1               5                   10                  15

Thr Cys Ala Gly Cys Ala Cys Cys Thr Thr Ala Thr Gly Cys Gly
            20                  25                  30


<210> SEQ ID NO 16
<211> LENGTH: 36
<212> TYPE: PRT
<213> ORGANISM: Unknown
<220> FEATURE:
<223> OTHER INFORMATION: Forward primer 5'
      GTAGGTGGATCCGGGTCATCCATAAATCTTGATTGG 3' (forward) used in Taq PCR

<400> SEQUENCE: 16

Gly Thr Ala Gly Gly Thr Gly Gly Ala Thr Cys Cys Gly Gly Gly Thr
1               5                   10                  15

Cys Ala Thr Cys Cys Ala Thr Ala Ala Ala Thr Cys Thr Thr Gly Ala
            20                  25                  30

Thr Thr Gly Gly
        35


<210> SEQ ID NO 17
<211> LENGTH: 36
<212> TYPE: PRT
<213> ORGANISM: Unknown
<220> FEATURE:
<223> OTHER INFORMATION: Reverse primer 5'
      CCCGTCATCCGGAAATGGTTAAGATCTATGCCCCGG 3' (reverse) used in Taq PCR

<400> SEQUENCE: 17

Cys Cys Cys Gly Thr Cys Ala Thr Cys Cys Gly Gly Ala Ala Ala Thr
1               5                   10                  15

Gly Gly Thr Thr Ala Ala Gly Ala Thr Cys Thr Ala Thr Gly Cys Cys
            20                  25                  30

Cys Cys Gly Gly
        35
```